United States Patent [19]
Hasegawa et al.

[11] Patent Number: 5,547,552
[45] Date of Patent: Aug. 20, 1996

[54] OXYGEN CONCENTRATION DETECTING APPARATUS

[75] Inventors: Jun Hasegawa; Shigenori Isomura, both of Kariya; Tomomichi Mizoguchi, Nagoya; Yasutaka Nakamori, Anjo, all of Japan

[73] Assignee: Nippondenso Co., Ltd., Kariya, Japan

[21] Appl. No.: 480,239

[22] Filed: Jun. 7, 1995

[30] Foreign Application Priority Data

Jun. 20, 1994 [JP] Japan .................................. 6-136816
Jun. 28, 1994 [JP] Japan .................................. 6-145910
Jun. 30, 1994 [JP] Japan .................................. 6-149098

[51] Int. Cl.$^6$ .................................................. G01N 27/26
[52] U.S. Cl. .......................... 204/406; 204/408; 204/425; 204/427; 204/401; 422/83; 422/98
[58] Field of Search .................................. 204/401, 406, 204/425, 427, 408; 422/83, 98

[56] References Cited

U.S. PATENT DOCUMENTS

| | | | |
|---|---|---|---|
| 4,543,176 | 9/1985 | Harada et al. | 204/406 |
| 4,626,338 | 12/1986 | Kondo et al. | 204/406 |
| 4,882,030 | 11/1989 | Suzuki et al. | 204/406 |
| 5,405,521 | 4/1995 | Nakamori et al. | 204/406 |

Primary Examiner—Bruce F. Bell
Attorney, Agent, or Firm—Cushman, Darby & Cushman

[57] ABSTRACT

To shorten the time during which oxygen concentration cannot be detected, the temperature of an oxygen concentration sensor is detected by negatively biasing the sensor using a bias control circuit. A microcomputer estimates a saturated current thereof at one time before the current flowing through the sensor section ends rising based on a current detected by a current detecting circuit at that time. Further, the sensor is positively biased right after the elapse of a negative bias voltage application period by the bias control circuit. The microcomputer determines the air-fuel ratio based on the current flowing through the sensor at that time. The period in which the negative bias is applied is variably set appropriately by the microcomputer in response to changes of engine temperature and intake air amount. Furthermore, to activate the sensor quickly, the temperature of the sensor section is detected and a heater is controlled based thereon.

41 Claims, 22 Drawing Sheets

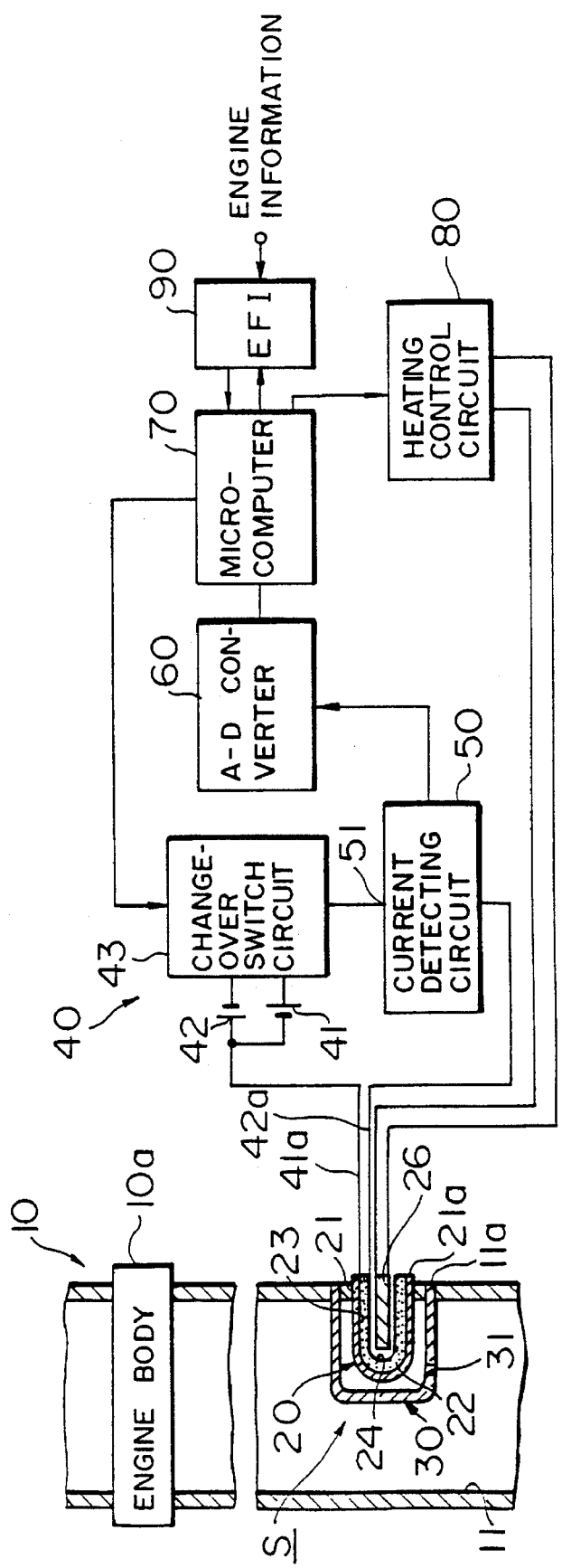

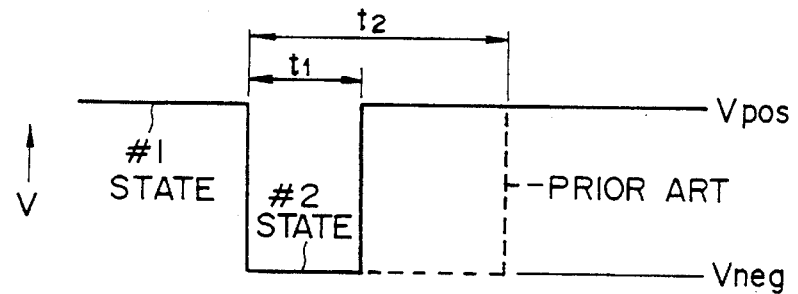
FIG. 5A1
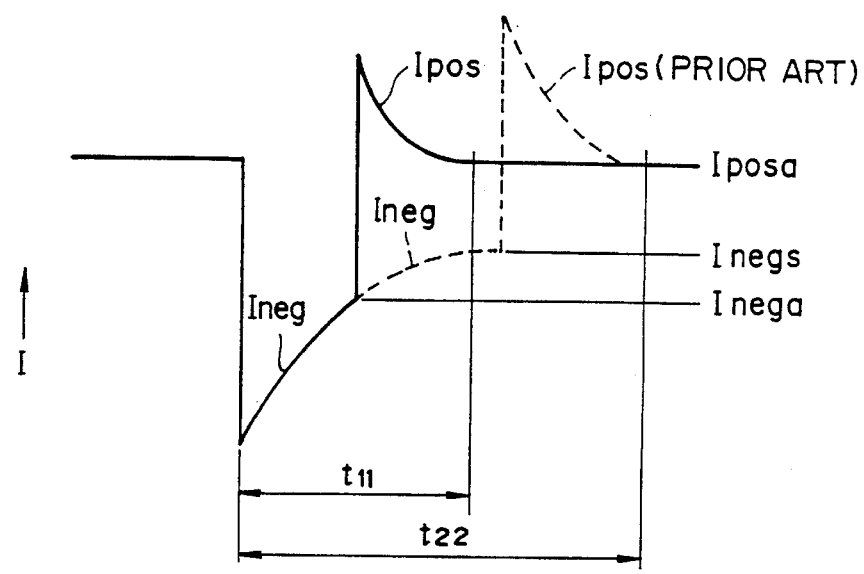
FIG. 5A2
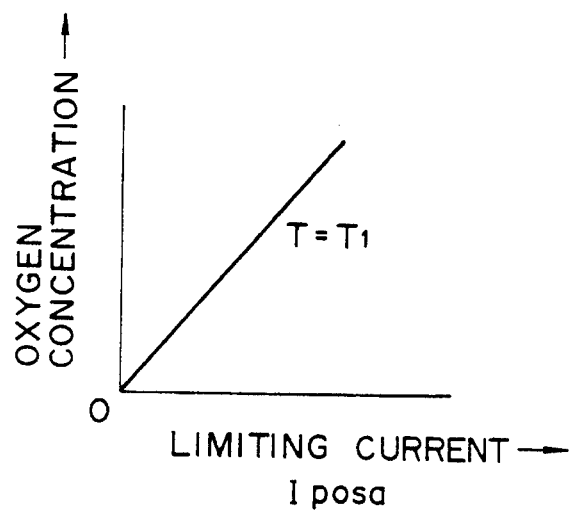
FIG. 5B

FIG.16
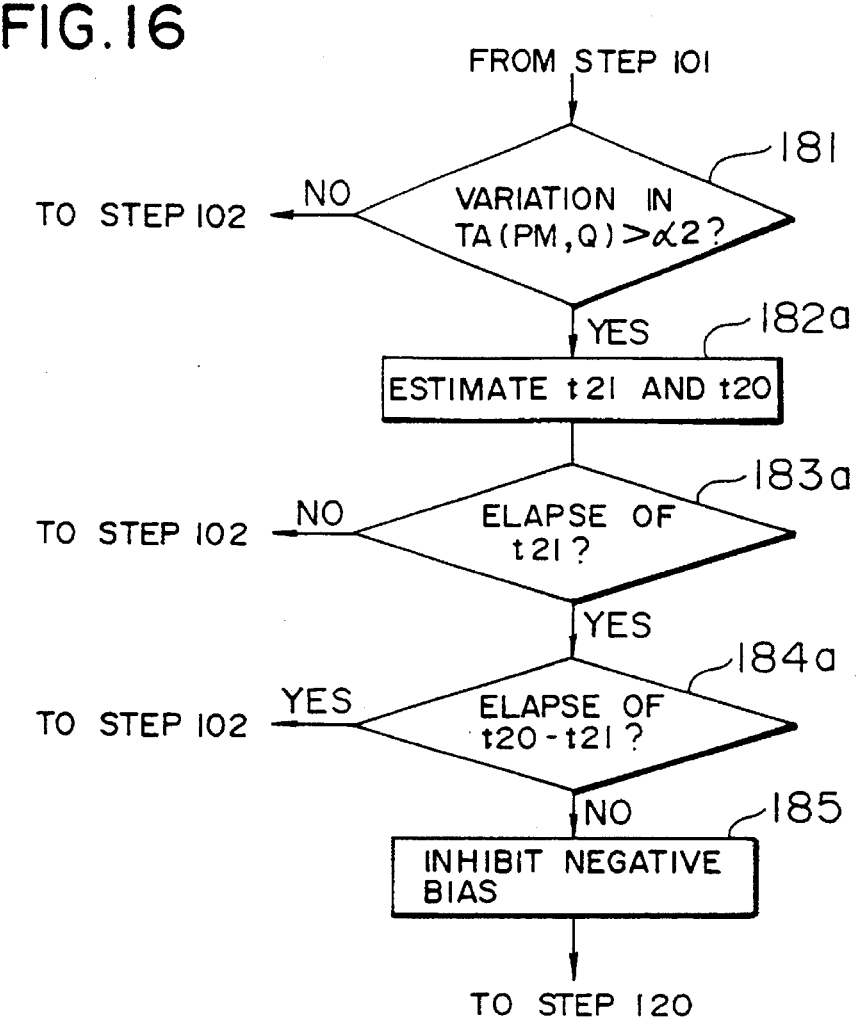
FIG.17A  TA
FIG.17B  A/F
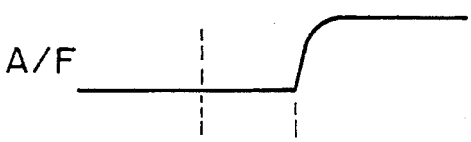
FIG.17C  I
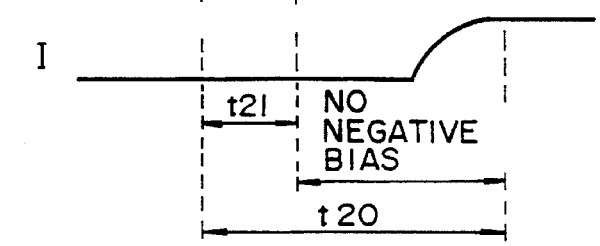

5,547,552

OXYGEN CONCENTRATION DETECTING APPARATUS

CROSS REFERENCE TO RELATED APPLICATION

This application is based on and claims priorities of Japanese Patent Applications No. 6-136816 filed on Jun. 20, 1994, No. 6-145910 filed on Jun. 28, 1994 and No. 6-149098 filed on Jun. 30, 1994, the contents of which are incorporated herein by reference.

BACKGROUND OF THE INVENTION

1. Field of the Invention

The present invention relates to an oxygen concentration detecting apparatus for detecting an air-fuel ratio, i.e. an oxygen concentration and the like, within the exhaust gas of an internal combustion engine and, more particularly, to an oxygen concentration detecting apparatus for detecting an oxygen concentration utilizing an oxygen sensor of a limiting current type.

2. Description of the Related Art

Hitherto, in an oxygen concentration detecting apparatus of this type, an internal electric resistance of an oxygen sensor of a limiting current type changes with temperature and a current-voltage characteristic that specifies the temperature, i.e. the internal resistance, of the oxygen sensor passes through an origin. The oxygen sensor is positively biased during a first period by a positive voltage and is then negatively biased during a second period by a negative voltage. The currents flowing through the oxygen sensor in the first and second periods are detected to determine an oxygen concentration on the basis of the current detected in the first period and to determine the internal electrical resistance of the oxygen sensor on the basis of the current detected in the second period, as shown in Japanese Patent Laid-Open No. 59-163556 (U.S. Pat. No. 4,543,176), for example. Then, an air-fuel ratio is detected stably on the basis of the detected oxygen concentration after accurately controlling the temperature of the oxygen sensor so as to maintain it in an active state by heating it so that the detected internal resistance becomes almost constant.

Further, the internal resistance and the temperature of the oxygen sensor correspond on a one-to-one basis. Restrictions on the usable temperature range and oxygen concentration measurable range are eliminated by detecting the internal resistance of the oxygen sensor, calculating a voltage to be applied to the oxygen sensor in response to the detected value of the internal resistance and applying the voltage to the oxygen sensor based on that calculation, as disclosed in Japanese Patent Publication Nos. 1-28905 (U.S. Pat. No. 4,626,338) and 1-25419 (U.S. Pat. No. 4,626,338).

In the apparatus constructed as described above, however, there has also been a problem in that because the above-mentioned second period is repeated uniformly, the air-fuel ratio can be determined only after the elapse of the second period and the period in which the air-fuel ratio can be determined is delayed even if the circumstance allows to stably determine the air-fuel ratio. Further, because the above-mentioned second period is repeatedly set regardless of a drop of the temperature of the oxygen sensor, the period in which the negative voltage is applied to the oxygen sensor does not necessarily coincide with the period in which the temperature of the oxygen sensor starts to drop. Accordingly, if the temperature of the oxygen sensor drops too much before the next period in which the negative voltage is applied after a condition in which the air-fuel ratio can be stably determined has been once brought about, it will take a long period of time before the air-fuel ratio can be stably determined, even if the temperature is controlled by applying the negative voltage as described above because the response of the oxygen sensor to the temperature is slow. In such a case, because the above-mentioned second period is set at a time necessary for the internal resistance of the oxygen sensor to be stabilized, the period in which the air-fuel ratio can be determined is delayed even further.

In the apparatus constructed as described above, there has been another problem in that the air-fuel ratio which is detected before the oxygen sensor has been activated is not necessarily credible. In consideration of the operation performance of the internal combustion engine right after its start, it is not necessary to detect an air-fuel ratio, which is likely to be inaccurate after the engine start. Rather, it is more important to raise the sensor temperature quickly to the activating temperature by controlling a heater.

SUMMARY OF THE INVENTION

Accordingly, it is a primary object of the present invention to solve the above-mentioned first drawback by considerably shortening the time in which the oxygen concentration cannot be detected with an oxygen concentration detecting apparatus by scheduling a timing for detecting an internal resistance and a timing for detecting an air-fuel ratio in accordance with the degree of need.

It is another object of the present invention to solve the above-mentioned second drawback by measuring an accurate oxygen concentration (air-fuel ratio) in a short time after starting the engine by forcibly continuing to apply a negative voltage until the oxygen sensor is activated and by detecting the sensor temperature and controlling the heater to raise the sensor temperature quickly to the sensor activating temperature.

It is a still another object of the present invention to solve the first drawback by considerably shortening the time in which oxygen concentration cannot be detected with the oxygen concentration detecting apparatus by detecting the oxygen concentration in a short time by estimating a current value after a convergence by a current value on the way of the convergence after the application of the positive bias.

As shown in FIG. 1A, according to a first aspect of the present invention, there is provided an oxygen concentration detecting apparatus comprising, in addition to an oxygen sensor of a limiting current type, voltage applying means, current detecting means, impedance detecting means and oxygen concentration detecting means, timing varying means for variably setting the timing for changing over the voltage applied to the oxygen sensor from the voltage applying means from the positive voltage to the negative voltage.

By constructing the detecting apparatus as described above, the timing for changing over the voltage applied to the oxygen sensor to the negative voltage may be variably set by the timing varying means, so that the period in which the positive voltage is applied to the oxygen sensor to detect the oxygen concentration may be prolonged by prolonging the temperature detecting interval in a state wherein the temperature of the oxygen sensor changes less.

As shown in FIG. 1B, according to a second aspect of the present invention, there is provided an oxygen concentration detecting apparatus comprising an oxygen sensor of a limiting current type, activation determining means, voltage applying means, negative voltage application continuing means, current detecting means, sensor temperature detecting means, oxygen concentration detecting means, a heater and heating control means for controlling the heating of the heater based on the sensor temperature detected by the sensor temperature detecting means.

By constructing the apparatus as described above, the negative voltage is applied continuously to the oxygen sensor by the negative voltage application continuing means through the voltage applying means until the oxygen sensor is determined to have been activated by the activation determining means. The sensor temperature of the oxygen sensor is detected by the sensor temperature detecting means on the basis of the current detected when the negative voltage is applied to the oxygen sensor. The heating of the heater is controlled by the heating control means on the basis of the sensor temperature detected by the sensor temperature detecting means to raise the sensor temperature quickly to the activating temperature. After that, when it is determined by the activation determining means that the oxygen sensor has been activated, the positive voltage is applied to the oxygen sensor and then the negative voltage is applied for a predetermined period of time to detect the oxygen concentration by the oxygen concentration detecting means on the basis of the current detected when the positive voltage is applied to the oxygen sensor and to detect the sensor temperature of the oxygen sensor by the sensor temperature detecting means on the basis of the current detected when the negative voltage is applied to the oxygen sensor for the predetermined period of time.

As shown in FIG. 1C, according to a third aspect of the present invention, there is provided an oxygen concentration detecting apparatus which differs from the first aspect in that it comprises a limiting current predicting means for predicting a limiting current after the convergence by a current detected on the way of the convergence after the application of the positive voltage to the oxygen sensor, and oxygen concentration detecting means for detecting the oxygen concentration on the basis of the predicted limiting current.

By constructing as described above, the positive voltage is applied and then the negative voltage is applied, by changing over to it, for the predetermined period of time to the oxygen sensor by the voltage applying means to detect the current flowing through the oxygen sensor due to the application of the voltage by the current detecting means and to detect a DC impedance of the oxygen sensor by the impedance detecting means on the basis of the current detected when the negative voltage is applied to the oxygen sensor for the predetermined period of time. Then, the limiting current after the convergence is predicted from the current detected on the way of the convergence after the application of the positive voltage to the oxygen sensor by the limiting current predicting means and the oxygen concentration is detected by the oxygen concentration detecting means on the basis of the predicted limiting current.

BRIEF DESCRIPTION OF THE DRAWINGS

The specific nature of the present invention, as well as other objects, uses and advantages thereof, will clearly appear from the description and from the accompanying drawings.

In the accompanying drawings:

FIG. 2 is a block circuit diagram showing an embodiment related to a first aspect;

FIGS. 5A1 and 5A2 are time charts showing waveforms of voltages applied to the sensor section and waveforms of currents flowing through the sensor section when negatively and positively biased, and FIG. 5B is a graph showing a relationship between an oxygen concentration and a limiting current;

FIG. 16 is a flowchart, showing the additional embodiment to be added to FIG. 4, for inhibiting the negative bias when the air-fuel ratio changes;

FIGS. 17A through 17C are time charts for explaining the operation of FIG. 16;

DETAILED DESCRIPTION OF THE PREFERRED EMBODIMENT

FIRST ASPECT

Figure 1A:
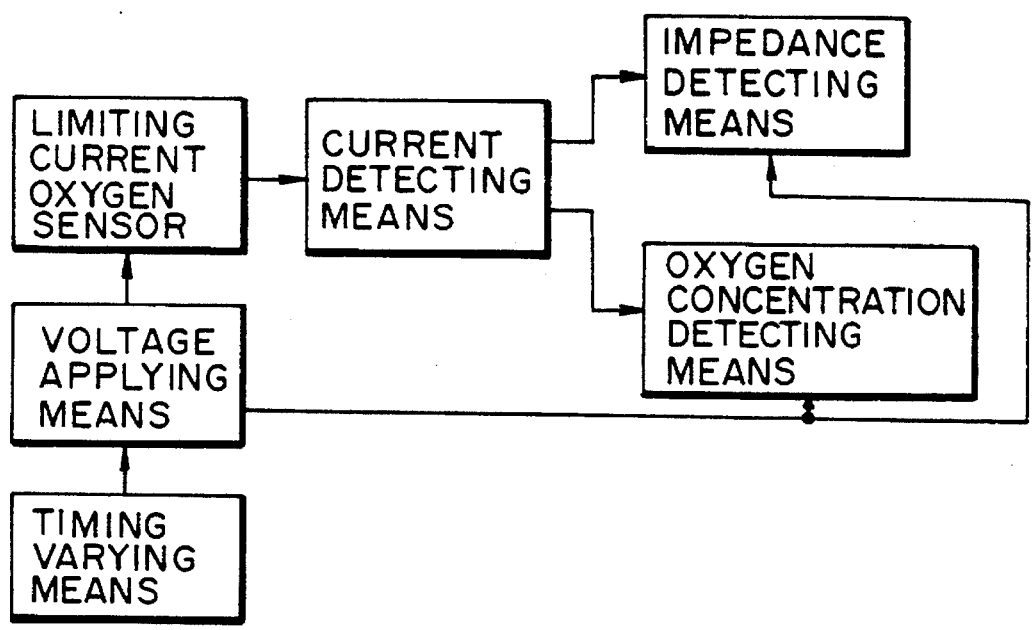
FIGS. 1A through 1C are block diagrams showing schematic diagrams of the present invention.

A first aspect of the present invention will be explained below with reference to FIG. 1A and FIGS. 2 through 19. FIG. 2 shows an oxygen concentration detecting apparatus of the present invention applied to an internal combustion engine 10. The oxygen concentration detecting apparatus comprises an oxygen sensor S of a limiting current type which is attached to an exhaust pipe 11 extending from an engine body 10a of the internal combustion engine 10. The oxygen sensor S comprises a sensor section 20 and a cover 30 having a cup shape section. The sensor section 20 is attached within a mounting hole 11a perforated through part of a circumferential wall of the exhaust pipe 11 at the basal end portion thereof and extends toward the inside of the exhaust pipe 11.

The sensor section 20 has, as is known well in the art, a diffusion resistant layer 21 having a cup shape section. The diffusion resistant layer 21 is attached within the mounting hole 11a of the exhaust pipe 11 at an opening end portion 21a thereof. The diffusion resistant layer 21 is formed by means of a plasma flame coating of $ZrO_2$ or the like. The sensor section 20 has a solid electrolyte layer 22 which is formed into a cup shape section by a sintered body of an oxygen ion conductive oxide and is homogeneously attached to the inner circumferential wall of the diffusion resistant layer 21 through an intermediary of an exhaust gas side electrode layer 23 having a cup shape section. An atmosphere side electrode layer 24 having a cup shape section is homogeneously secured on the internal surface of the solid electrolyte layer 22. In the apparatus described above, the exhaust gas side electrode layer 23 and the atmosphere side electrode layer 24 are formed to be fully porous by a noble metal, such as platinum, having a high catalytic activity by chemical plating or the like. An area and thickness of the exhaust gas side electrode layer 23 are around 10 to 100 $mm^2$ and 0.5 to 2.0 microns, respectively, and those of the atmosphere side electrode layer 24 are more than 10 $mm^2$ and around 0.5 to 2.0 microns, respectively.

The sensor section 20 constructed as described above generates a rich or lean concentration dependent electromotive force at a stoichometric point and a limiting current in response to the oxygen concentration on the lean side of the stoichometric air-fuel ratio. At that time, the limiting current which corresponds to the oxygen concentration is determined by the area of the exhaust gas side electrode layer 23, the thickness and the porosity and the average pore diameter of the diffusion resistant layer 21. Although the sensor section 20 detects the oxygen concentration with a linear characteristic, its active region cannot be controlled solely by heating by the exhaust gas of the internal combustion engine because it needs a high temperature of more than about 650° C. to activate the sensor section 20 and its active temperature range is narrow. Due to that, a heater 26, described later, is utilized to control the heating. It should be noted that a concentration of carbon monoxide (CO) which is an unburnt gas changes almost linearly to the air-fuel ratio in the rich side from the stoichometric air-fuel ratio and a limiting current corresponding to that is generated.

A voltage-current characteristic of the sensor section 20 having a parameter of the temperature of the sensor section 20 will be explained hereinbelow. This voltage-current characteristic shows that a relationship between a current flowing through the solid electrolyte layer 22 of the sensor section 20, which is proportional to the detected oxygen concentration (air-fuel ratio) of the oxygen sensor S, and a voltage applied to the solid electrolyte layer 22 is linear. Then, when the sensor section 20 is in the active state at temperature T=T1, it shows a stable state as shown by a characteristic graph L1 shown by the solid line in FIG. 3B. Here, the linear portion of the characteristic graph L1, which is parallel to a voltage axis V, specifies the limiting current of the sensor section 20. Then, the increase/decrease of this limiting current corresponds to the decrease/increase (i.e. lean or rich) of the air-fuel ratio. When the temperature T of the sensor section 20 is at T2, which is lower than T1, the current-voltage characteristic is specified by a characteristic graph L2 shown by the broken line in FIG. 3B. Here, a linear portion of the characteristic graph L2, which is parallel to the voltage axis V, specifies the limiting current of the sensor section 20 at T=T2 and this limiting current corresponds almost with the limiting current of the characteristic graph L1.

When a positive applied voltage Vpos is applied to the solid electrolyte layer 22 of the sensor section 20, the current flowing through the sensor section 20 becomes a limiting current Ipos (see point P1 in FIG. 3B) in the characteristic graph L1. When a negative applied voltage Vneg is applied to the solid electrolyte layer 22 of the sensor section 20, the current flowing through the sensor section 20 becomes a negative current Ineg which is not dependent on the oxygen concentration but is proportional only to temperature and which is specified by a point P2. Accordingly, the sensor section 20 may be kept in the active state by controlling the heating of the heater 26 by utilizing the current Ineg at this time to make the internal resistance (DC impedance) of the sensor section 20, i.e. the sensor temperature, constant.

Referring to FIG. 2 again, the sensor section 20 comprises the heater 26, which is accommodated within the atmosphere side electrode layer 24, for heating the atmosphere side electrode layer 24, the solid electrolyte layer 22, the exhaust gas side electrode layer 23 and the diffusion resistant layer 21 by its exothermic energy. Here, the heater 26 has a heating capacity sufficient to activate the sensor section 20. The cover 30 covers the sensor section 20 and is attached to a portion of the circumferential wall of the exhaust pipe 11 at its opening section. A small hole 31 is perforated through a part of the circumferential wall of the cover 30 so as to communicate the outside of the cover 30 with the inside thereof. Thereby, the cover 30 thermally shields the sensor section 20 while preventing the sensor section 20 from coming into direct contact with the exhaust gas.

As shown in FIG. 2, the oxygen concentration detecting apparatus comprises a bias control circuit 40. The bias control circuit 40 includes a DC power source for positive bias 41, a DC power source for negative bias 42 and a change-over switch circuit 43. The DC power source 41 is connected to one end of the exhaust gas side electrode layer 23 via a lead wire 41a by its negative side electrode and the DC power source 42 is connected to one end of the exhaust gas side electrode layer 23 via the lead wire 41a by its positive side electrode. The change-over switch circuit 43 connects only the positive side electrode of the DC power source 41 to an input terminal 51 of a current detecting circuit 50 in its first change-over state and connects only the negative side electrode of the DC power source 42 to the input terminal 51 of the current detecting circuit 50 in its second change-over state. Then the current is connected from the input terminal 51 to the atmosphere side electrode layer 24 via the current detecting circuit 50 and a lead wire 42a. Accordingly, when the change-over switch circuit 43 is in the first change-over state, the DC power source 41 positively biases the solid electrolyte layer 22 and current flows in the positive direction through the solid electrolyte layer 22. On the other hand, when the change-over switch circuit 43 is in the second change-over state, the DC power source 42 negatively biases the solid electrolyte layer 22 and current flows in the negative direction through the solid electrolyte layer 22. Here, the terminal voltage of each of the DC power sources 41 and 42 corresponds to the applied voltages Vpos and Vneg described above, respectively.

The current detecting circuit 50 detects the current flowing from the atmosphere side electrode layer 24 of the sensor section 20 to the change-over switch circuit 43 or that flowing in the opposite direction, i.e. the current flowing through the solid electrolyte layer 22, and outputs it to an A-D converter 60. The A-D converter 60 converts the detected current from the current detecting circuit 50 into digital data and outputs this file to a microcomputer 70. The microcomputer 70 executes a computer program following the flowchart shown in FIG. 4 in cooperation with the A-D converter 60. During the execution, it implements an arithmetic operation necessary for driving and controlling a heating control circuit 80 and an electronically-controlled fuel injection system (hereinafter abbreviated as EFI) 90. The above-mentioned computer program is stored in a ROM of the microcomputer 70 beforehand. The heating control circuit 80 controls the heating of the heater 26 in response to the sensor temperature of the oxygen sensor S under the control of the microcomputer 70. The heating control circuit 80 controls the fuel injection in response to information on the internal combustion engine 10 such as an amount of exhaust gas, number of rotation, flow rate of intake air, negative pressure of intake pipe, and temperature of cooling water, etc. under the control of the microcomputer 70.

Figure 3A:
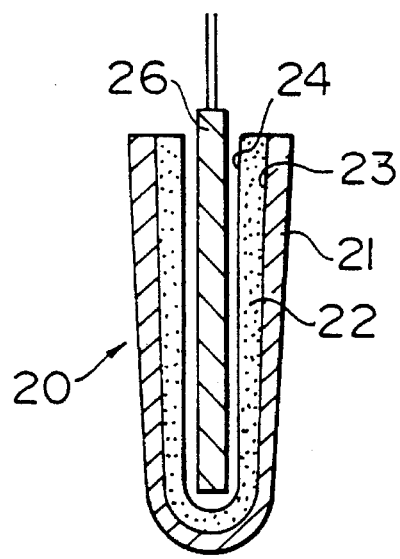
FIG. 3A is an enlarged section view of a sensor section of an oxygen sensor in FIG. 2
Figure 3B:
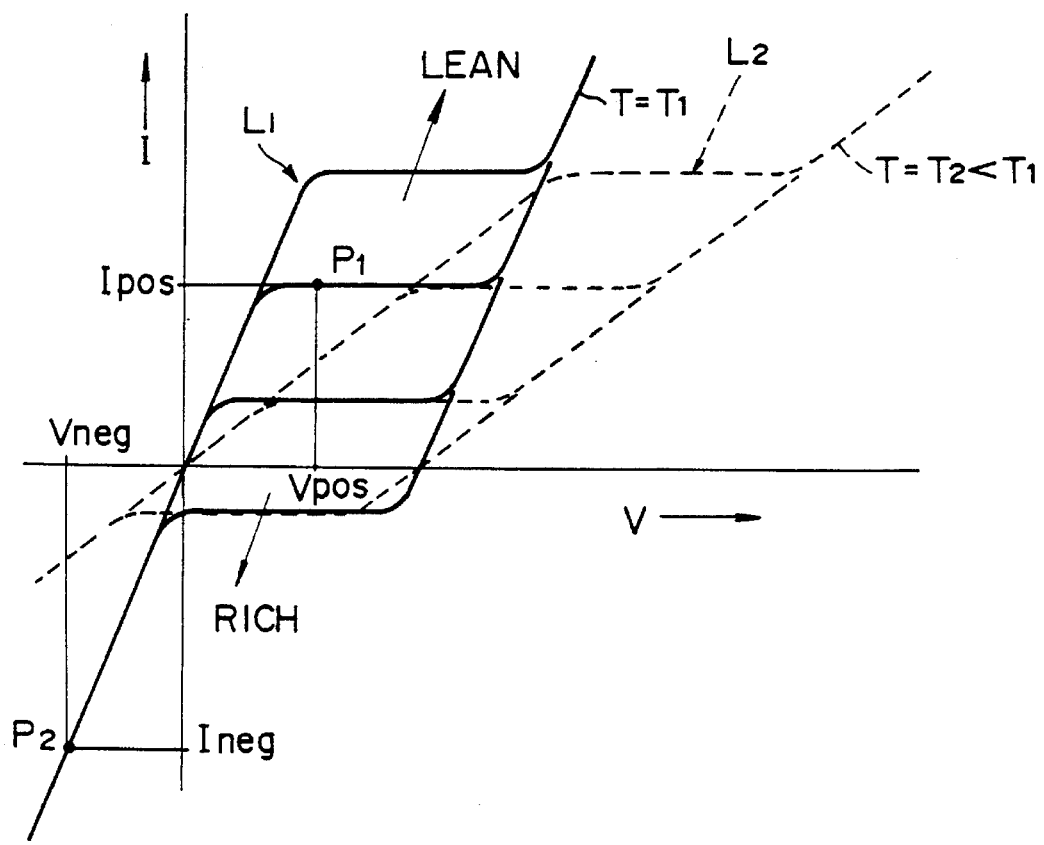
FIG. 3B is a graph showing a limiting current-voltage characteristic in the oxygen sensor with a parameter of temperature.

Since FIGS. 2, 3A and 3B are applicable also to second and third aspects of the present invention, the bias control circuit 40 will be explained later in detail with reference to FIG. 28.

First Embodiment

Figure 4:
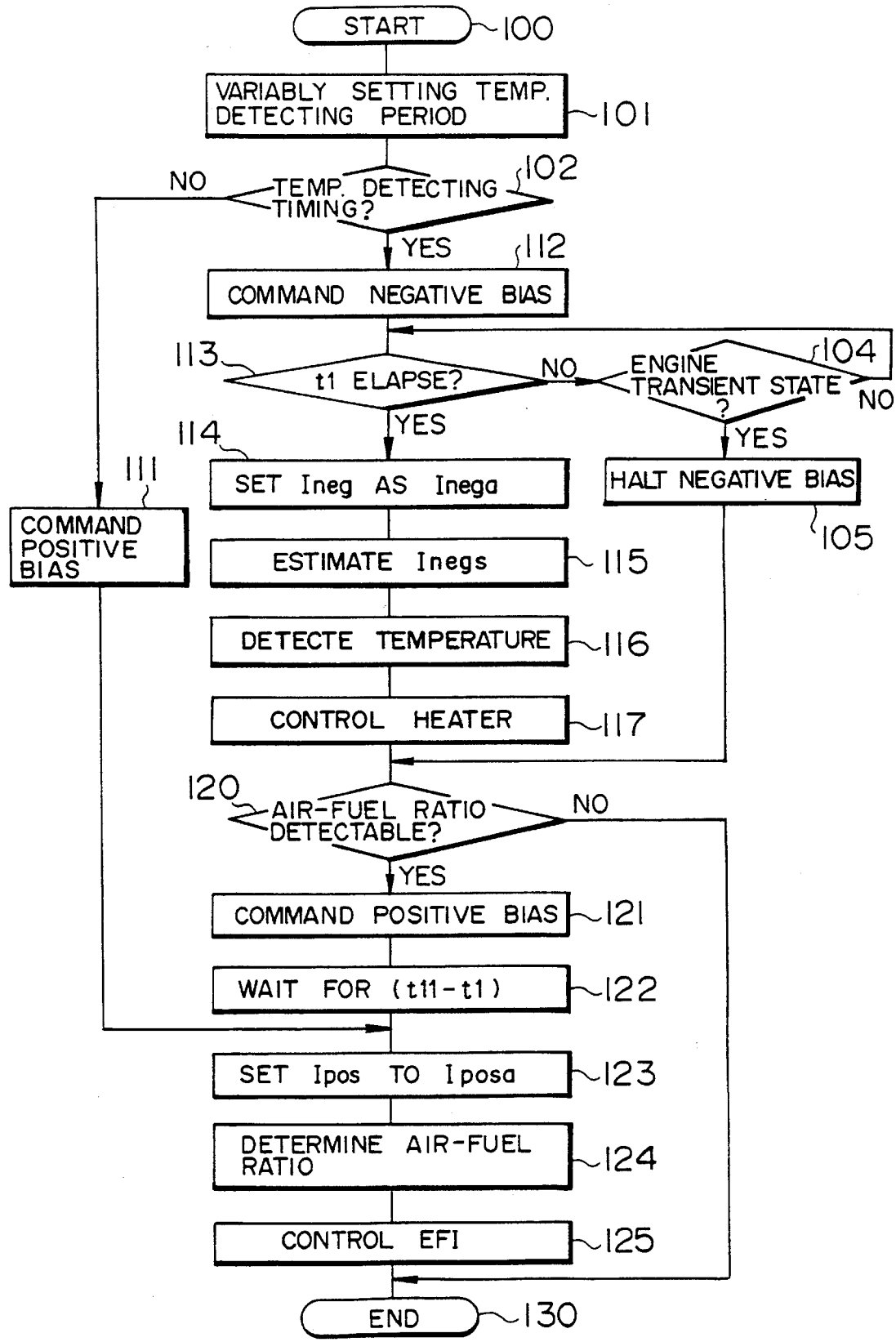
FIG. 4 is a flowchart showing the operation of a microcomputer in FIG. 2.

Assume that in the embodiment constructed as described above, the microcomputer 70 repeats the execution of the computer program after starting to execute the computer program at Step 100 following to the flowchart in FIG. 4. Assume also that the oxygen sensor S is in the active state and is stable in the present stage. Then, after variably setting a temperature detecting period on the basis of the warming up state and operation state of the internal combustion engine in Step 101, determined in Step 102 whether it is the temperature detecting timing is set in Step 101 or not. If it is not the temperature detecting period, the determination of "NO" is repeated in Step 102.

In such a state, the microcomputer 70 advances the computer program to Steps 111 and 123. In Step 111, the microcomputer 70 outputs a positive bias command, which is necessary for applying a positive applied voltage Vpos to the sensor section 20, to the change-over switch circuit 43 of the bias control circuit 40. Although the applied voltage Vpos may be a constant value here, it is preferable to change the applied voltage Vpos in response to the sensor temperature and oxygen concentration (i.e. to set the applied voltage Vpos at a higher value when the sensor temperature is low as compared with a case when the sensor temperature is high and to set the applied voltage Vpos at a higher value when the oxygen concentration is high (air-fuel ratio is lean) as compared with a case when the oxygen concentration is low (air-fuel ratio is rich)), because the applied voltage Vpos necessary for detecting the limiting current changes in response to the sensor temperature of the oxygen sensor S and the oxygen concentration as shown in FIG. 3B. Then, in response to the positive bias command from the microcomputer 70, the change-over switch circuit 43 is put into the first change-over state and connects the positive side electrode of the DC power source 41 to the input terminal 51 of the current detecting circuit 50. Due to that, the current Ipos from the DC power source 41 flows through the current detecting circuit 50, the lead wire 42a, the atmosphere side electrode layer 24, the solid electrolyte layer 22, the exhaust gas side electrode layer 23 and the lead wire 41a as the limiting current.

Next, the current detecting circuit 50 detects the flow-in current Ipos and the A-D converter 60 converts the detected flow-in current Ipos into digital to output to the microcomputer 70. Then, the microcomputer 70 inputs the converted current Ipos and sets as a decrease ending current Iposa in Step 123 and determines the oxygen concentration, i.e. the air-fuel ratio, in response to the decrease ending current Iposa, i.e. the limiting current, on the basis of the oxygen concentration-limiting current data shown in FIG. 5B. Note that the oxygen concentration-limiting current data in FIG. 5B has been stored in the ROM of the microcomputer 70 beforehand as data which specifies a linear relationship between the oxygen concentration within the exhaust gas, i.e. the air-fuel ratio, and the limiting current of the sensor section 20. When the air-fuel ratio is thus determined, the microcomputer 70 implements the arithmetic operation necessary for controlling the fuel injection of the EFI 90 taking the determined air-fuel ratio into account in Step 125. Thereby, the EFI 90 controls the fuel to be injected into the internal combustion engine 10 on the basis of the arithmetic operation.

Figure 1B:
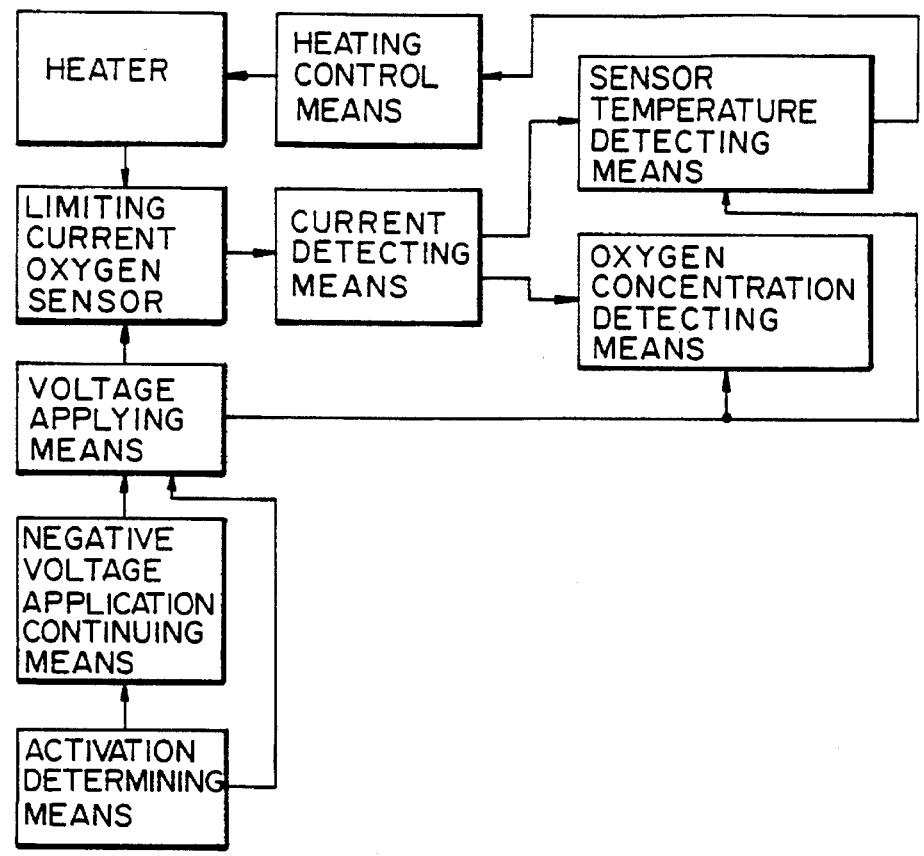
Figure 1C:
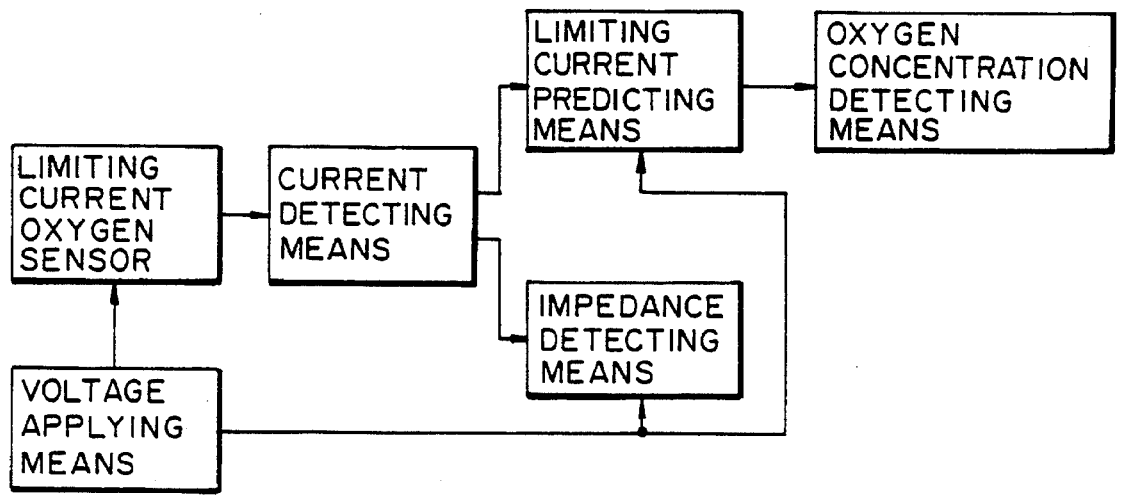

In such state, the microcomputer 70 determines to be "YES" in Step 102 judging that it is the temperature detecting period set in Step 101 and outputs a negative bias command necessary for applying a negative applied voltage Vneg to the sensor section 20 to the change-over switch circuit 43 of the bias control circuit 40 (see FIG. 5A1). Then, in response to the negative bias command from the microcomputer 70, the change-over switch circuit 43 is put into the second change-over state and connects the negative side electrode of the DC power source 42 to the input terminal 51 of the current detecting circuit 50. Thereby, the current Ineg (see the solid line in FIG. 5A1) from the DC power source 42 starts to flow through the lead wire 41a, the exhaust gas side electrode layer 23, the solid electrolyte layer 22, the atmosphere side electrode layer 24 of the sensor section 20, the lead wire 42a and the current detecting circuit 50.

After the arithmetic operation in Step 112 described above, the microcomputer 70 determines whether a predetermined time t1 has passed or not to wait for the predetermined time t1 in Step 113. Here, the predetermined time t1 is defined as follows. That is, the current Ineg increases exponentially as shown by the solid and broken lines in FIG. 5A2 after being negatively biased to the sensor section 20. Therefore, if the current Ineg is detected waiting for the time when the current Ineg saturates like the prior art, the air-fuel ratio determining time thereafter is also delayed. Then, a value Inega at one time in the process of the increase of the current Ineg is utilized to estimate the saturation current Inegs of the current Ineg at that time without waiting for the time when the current Ineg saturates. Thereby, the air-fuel ratio determining time is obviously made early. Then, an adequate time until the tendency of changes of the current Ineg is maintained relatively highly from when it is negatively biased to the sensor section 20 is selected to be the predetermined time t1 and is stored in the ROM of the microcomputer 70 beforehand.

When it is determined to be "NO" in Step 113, it is determined in Step 104 whether the variation of the pressure of the intake pipe or the amount of intake air is more than a predetermined value or not, i.e. whether the engine is in a transient state or not.

When it is determined to be "NO" in Step 104, this process is repeated returning to Step 113. When it is determined to be "YES" in Step 104, the negative bias command is halted in Step 105 and the process advances to Step 120.

When the microcomputer 70 thus finishes waiting for the time t1 in Step 113, it sets the converted current Ineg from the A-D converter 60 as the current Inega in Step 114 and estimates the saturation current Inegs in response to the current Inega and on the basis of a transient phenomenon equation representing a relationship between the current Ineg and the applied voltage Vneg in Step 115. The transient phenomenon equation is formed of the time when the sensor section 20 is negatively biased as the initial condition and is stored in the ROM of the microcomputer 70 beforehand. After that, the microcomputer 70 detects the temperature of the sensor section 20 in Step 116 on the basis of the estimated saturation current-temperature characteristic data in response to the estimated saturation current Inegs. The estimated saturation current-temperature characteristic data is stored in the ROM of the microcomputer 70 beforehand as data representing a direct proportional relationship between the estimated saturation current |Inegs| and the temperature of the sensor section 20.

When the temperature of the sensor section 20 is thus detected, the microcomputer 70 implements an arithmetic operation in Step 117 to heat and control the heater 26 so as to raise and maintain the temperature detected in Step 116 to a temperature T1 (see characteristic graph L1). Then, the heating control circuit 80 heats and controls the heater 26 on the basis of the heating control arithmetic operation implemented by the microcomputer 70. Thereby, even if the temperature of the sensor section 20 drops temporarily, it is returned to the temperature T1 quickly.

Due to that, judging that the air-fuel ratio may be stably detected, the microcomputer 70 determines to be "YES" in Step 120 and advances the computer program to Step 121. Then, the microcomputer 70 outputs to the bias control circuit 40 a positive bias command which is necessary for applying the positive applied voltage Vpos to the sensor section 20. Then, the bias control circuit 40 applies the applied voltage Vpos from the DC power source 41 to the sensor section 20 similarly to the case described above. It means that the applied voltage Vpos is applied to the sensor section 20 right after the elapse of the above-mentioned predetermined period t1. Thereby, the current Ipos from the DC power source 41 starts to flow through the lead wire 41a, the exhaust gas side electrode layer 23, the solid electrolyte layer 22, the atmosphere side electrode layer 24 of the sensor section 20, the lead wire 42a and the current detecting circuit 50 as a limiting current. In other words, as shown in FIG. 5A, the current Ineg flowing through the sensor section 20 is inverted and rises to become the current Ipos right after the elapse of the predetermined period t1 and then starts to exponentially decrease thereafter as shown by the solid line in the figure.

When the arithmetic operation in Step 121 is finished as described above, the microcomputer 70 waits for a predetermined time (t11–t1) (see FIG. 5A) in the next Step 122. Note that t11 represents the time from when the current Ineg started to flow as described above till when the current Ipos, which started to flow right after the elapse of the predetermined period t1 ends to decrease exponentially. The predetermined time (t11–t1) is defined based on the following ground.

At first, the case similar to the prior art in which the sensor section 20 is positively biased by applying the applied voltage Vpos when the current Ineg changes exponentially as shown by the solid line in FIG. 5A2 and saturates as shown by the broken line in FIG. 5A2 is compared with the case like the present embodiment in which the applied voltage Vpos is applied to the sensor section 20 right after the elapse of the predetermined period t1 to positively bias it (the solid line in FIG. 5A1). Note that the time necessary for the current Ineg to saturate in the prior art case is represented by t2 as shown in FIGS. 5A1 and 5A2.

The value at which the current Ipos ends to decrease as the applied voltage Vpos is applied goes upon a physical phenomenon intrinsic to the sensor section 20 and is almost the same in the both cases of the prior art and the first embodiment. Accordingly, when the time when the current Ipos ends to decrease exponentially in the prior art case is represented by t22 as shown in FIG. 5A2, the time when the current Ipos starts to flow in the case of the first embodiment (the solid line shown in FIG. 5A2) is earlier than the time when the current Ipos starts to flow in the prior art case (the broken line shown in FIG. 5A2) by a time (t2–t1) and in response to that, the time when the current Ipos ends to decrease in the case of the first embodiment is earlier than the time when the current Ipos ends to decrease in the prior art case. Further, the time when the current Ipos starts to flow in the first embodiment corresponds to one time on the way of the increase of the current Ineg and the time when the current Ipos starts to flow in the prior art case corresponds to the time when the current Ineg ends to increase. Thus, the oxygen concentration accumulated around the exhaust gas side electrode layer 23 during the negative bias period becomes smaller as compared with the prior art. Due to that, the leading edge peak level of the current Ipos becomes low and the time constant when the current Ipos decreases becomes smaller and decreases more rapidly. The degree of these two effects depends on a feed charge amount during the negative bias period. That is, when the charge amount is reduced by shortening t1, the above-mentioned two become small and t11 becomes short further. Accordingly, when the time from when the current Ineg starts to flow till when the current Ineg ends to decrease in the prior art case is represented by t22 as shown in FIG. 5A2, the time is made earlier by (t22–t11). Then, the predetermined time (t11–t1)

is set and is stored in the ROM of the microcomputer 70 beforehand.

After waiting for the time thus in Step 122, the microcomputer 70 inputs a converted current Ipos right after the elapse of the predetermined time t11 from the A-D converter 60 to set as the decrease-ending current Iposa in Step 123 and determines the oxygen concentration, i.e. air-fuel ratio, in response to the decrease-ending current Iposa, i.e. the limiting current, on the basis of the above oxygen concentration-limiting current data (see FIG. 5B) in Step 124. When the air-fuel ratio is thus determined, the microcomputer 70 implements the arithmetic operation, which is necessary for controlling the fuel injection of the EFI 90 taking the air-fuel ratio into consideration, in Step 125. Thereby, the EFI 90 controls the fuel injection to the internal combustion engine 10 on the basis of the arithmetic operation.

As described above, in determining the temperature of the sensor section 20, the saturation current Inegs is estimated at one time before the current Ineg, which flows through the sensor section 20, ends to rise after the sensor section 20 has been negatively biased by the applied voltage Vneg (when the predetermined time t1 elapsed) by the current Inega at that time, so that the time when the air-fuel ratio can be determined after that may be quickly brought forward.

Further, because the sensor section 20 is positively biased by the applied voltage Vpos right after the elapse of the predetermined time t1 and the air-fuel ratio is determined when the current Ipos which flows through the sensor section 20 by the positive bias ends to decrease, i.e. when the predetermined time (t11–t1) elapses, by the current Iposa at that time, the air-fuel ratio can be quickly determined as compared with the prior art. Here, as described above, the leading edge peak level of the current Ipos in the case of the first embodiment is maintained relatively low as compared with that of the current Ipos in the prior art case and the current Ipos in the case of the present embodiment rapidly decreases as compared with the current Ipos in the prior art case, so that the air-fuel ratio can be determined more quickly. It is also possible to estimate the value Iposa at which the current Ipos ends to decrease in the middle of the decrease of Ipos to detect the change of the air-fuel ratio more quickly.

Although the sensor section 20 is positively biased by the applied voltage Vpos right after the elapse of the predetermined time t1 in the first embodiment described above, the present invention is not confined only to that, and it is possible to positively bias the sensor section 20 by the applied voltage Vpos after the elapse of the predetermined time t1 and before the elapse of the predetermined time t11.

Second Embodiment

A second embodiment of the present invention will be explained hereinbelow. While the current Ineg is detected by measuring the value Inega at one time in the process of the increase of the current Ineg in estimating the saturation current Inegs of the current Ineg in the above-mentioned first embodiment, the second embodiment is characterized in that the saturation current Inegs of the current Ineg is estimated by measuring three times the value Inega in the process of increase of the current Ineg. Thus, the saturation current Inegs may be estimated more accurately.

Figure 6A:
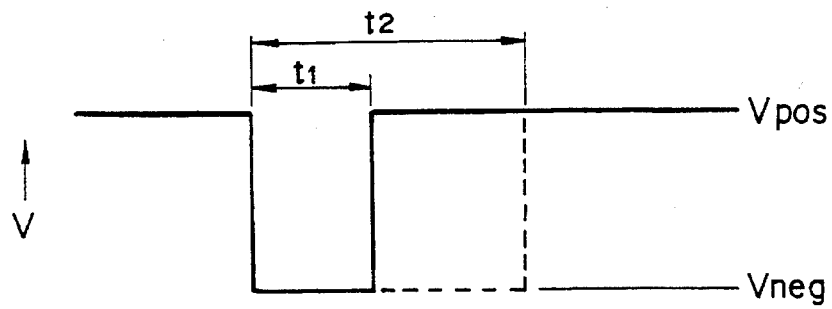
FIGS. 6A and 6B are time charts showing waveforms of voltages applied to the sensor section and waveforms of currents flowing through the sensor section when negatively and positively biased, similar to FIGS. 5A1, 5A2 and 5B.
Figure 6B:
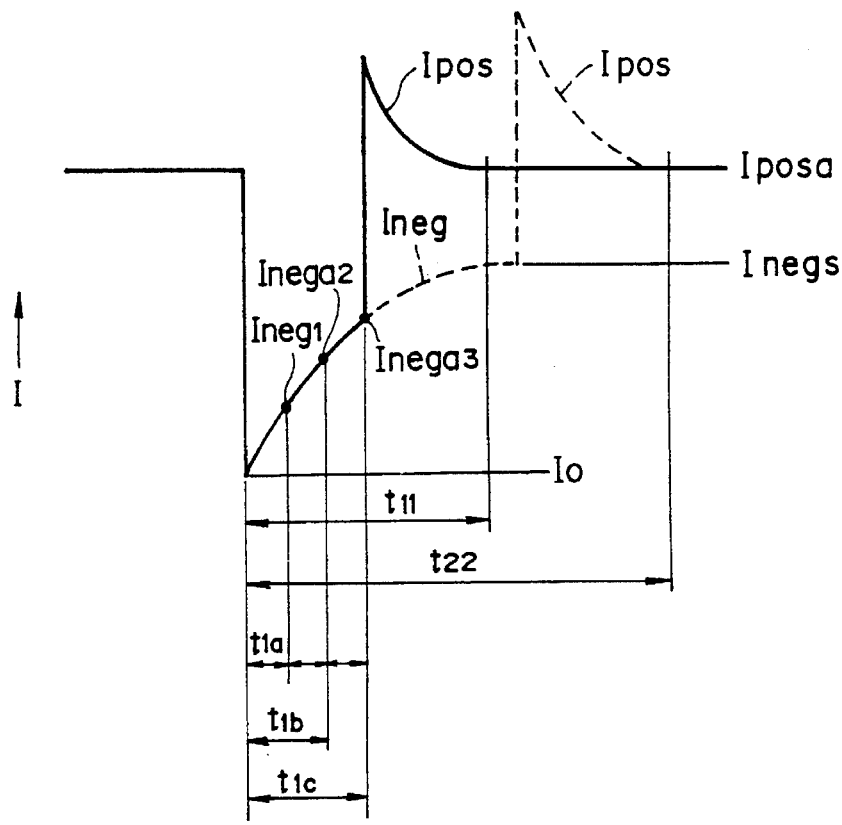

FIGS. 6A and 6B show, similarly to FIGS. 5A1 and 5A2, voltage V applied to the sensor section 20 and current I flowing through the sensor section 20 at that time. In FIG. 6, the current Ineg which flows when the applied voltage V is changed over from Vpos to Vneg changes exponentially as expressed by the following equation wherein ($I_0$) represents a peak current value, (Ineg) a saturated current value (converged current value) and (T) a time constant:

$$Ineg = Inegs + (I_0 - Inegs)e^{-t/T} \quad (1)$$

When the peak current value $I_0$, saturated current value (converged current value) Inegs and time constant T are unknown respectively, it is necessary to detect current values at three points on the Ineg curve Inega1, Inega2 and Inega3 in order to find Inegs. Then, Ineg is found by obtaining a solution of the following simultaneous equations from the current values detected at the three points:

$$Inega1 = Inegs + (I_0 - Inegs)e^{-t1a/T}$$
$$Inega2 = Inegs + (I_0 - Inegs)e^{-t1b/T} \quad (2)$$
$$Inega3 = Inegs + (I_0 - Inegs)e^{-t1c/T}$$

Here, Inega1, Inega2 and Inega3 are values of the current value Ineg after times t1a, t1b and t1c from when the applied voltage V is changed over from Vpos to Vneg.

For example, when it is assumed as t1a=0 and t1b=t1c–t1b to simplify the calculation and when those values are substituted for Equation (2), Inegs can be found by the following equation:

$$Inegs = (Inega2^2 - Inega3 \times Inega1)/(2 \times Inega2 - Inega3 - Inega1) \quad (3)$$

Next, the operation of the second embodiment will be explained with reference to a flowchart in FIG. 7. The second embodiment is different from the first embodiment described above in that the steps from Step 113 through Step 115 in FIG. 4 are replaced with steps from Step 113a through Step 115 in FIG. 7. Accordingly, since steps from Step 100 through Step 112 are the same with those in the first embodiment, an explanation thereof will be omitted here.

After the arithmetic operation in Step 112, the microcomputer 70 waits for the predetermined time t1a at Step 113a. Ending to wait for the time in Step 113a, the microcomputer 70 detects the current value in Step 114a and sets the converted current Ineg from the A-D converter 60 as the current Inega1. After that, the microcomputer 70 waits for the predetermined time t1b–t1a in Step 113b. Ending to wait for the time in Step 113b, the microcomputer 70 detects the current value in Step 114b and sets the converted current Ineg from the A-D converter 60 as the current Inega2. Next, the microcomputer 70 waits for the predetermined time t1c–t1b in Step 113c.

Ending to wait for the time in Step 113c, the microcomputer 70 detects the current value in Step 114c and sets the converted current from the A-D converter 60 as the current Inega3. After that, the microcomputer 70 calculates the saturation current Inegs based on the simultaneous equations (2) described above in Step 115. The simultaneous equations (2) are formed of the time when the negative bias is applied as the initial condition and is stored in the ROM of the microcomputer 70 beforehand. After that, the microcomputer 70 determines the temperature of the sensor section 20 in Step 116 in response to the saturation current Inegs found in Step 115 based on the saturation current-temperature characteristic data. Since steps from Step 117 through Step 300 are the same with those in the first embodiment, an explanation thereof is omitted here.

As described above, the second embodiment is characterized in that the saturation current Inegs of the current Ineg is estimated by measuring the value Inega of one time in the process of increase of the current Ineg three times and that thereby the saturation current Inegs can be estimated more accurately.

Step 101

Figure 9A:
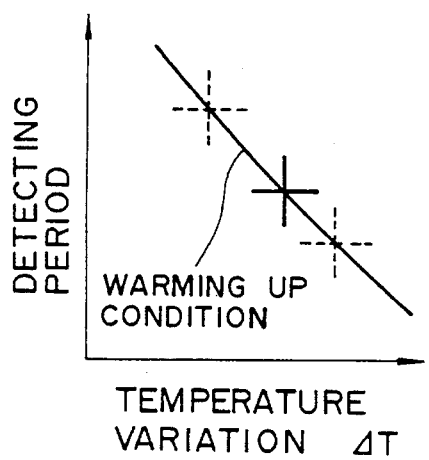
FIGS. 9A and 9B are graphs showing a detection period map 1 for a warming up state and a detection period map 2 with regard to different operating states.

The detail of Step 101 for variably setting a temperature detecting period in the first and second embodiments (FIGS. 4 and 7) described above will be explained with reference to FIG. 8 hereinbelow. At first, it is determined in Step 151 whether a predetermined time ta during which an engine temperature is stabilized has passed or not (or whether the sensor temperature is more than a predetermined temperature or not) after starting the internal combustion engine. When the predetermined time ta has not passed yet, the process is advanced to Step 152 to detect a variation $\Delta T$ of the sensor temperature of the oxygen sensor S determined in Step 116 in FIGS. 4 or 7. Then, in Step 153, the detecting period, which corresponds to the variation $\Delta T$ of the sensor temperature, is decided from a map 1 of the variation $\Delta T$ of the sensor temperature which is one of the engine warming up conditions and the detecting period which are stored in the ROM of the microcomputer 70 as shown in FIG. 9A. This map 1 is set so that the larger the variation $\Delta T$ of the sensor temperature, the shorter the detecting period becomes.

Figure 9B:
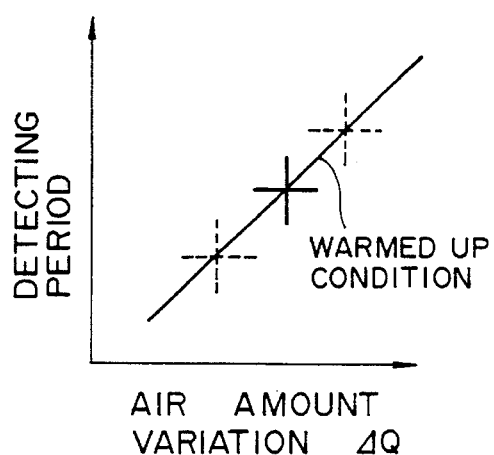

In the case when the predetermined time ta has passed after starting the internal combustion engine, a variation $\Delta Q$ of an intake air amount Q of the internal combustion engine is detected in Step 154. Then in Step 155, the detecting period, which corresponds to the variation $\Delta Q$ of the intake air amount Q, is decided from a map 2 of the variation $\Delta Q$ of the intake air amount Q which is one of changes of engine operation state and the detecting period which are stored in the ROM of the microcomputer 70 beforehand as shown in FIG. 9B. This map 2 is set so that the detecting period becomes longer as compared to the map 1 and so that the larger the variation $\Delta Q$ of the intake air amount Q, the longer the detecting period becomes.

Figure 10A:
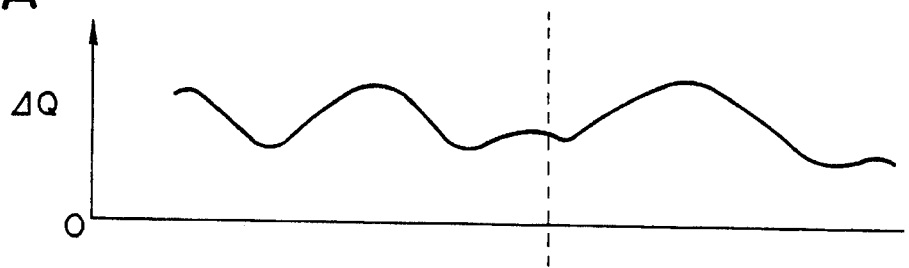
FIGS. 10A and 10B are time charts for explaining the operation of FIG. 8.
Figure 10B:
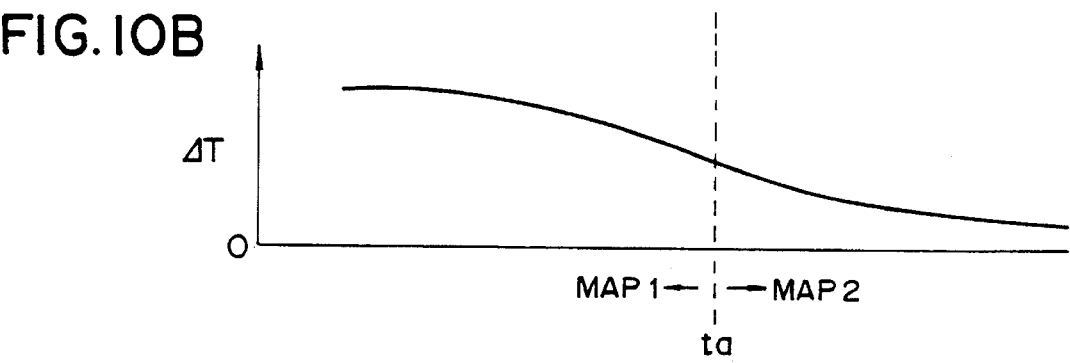

Thereby, as shown in FIGS. 10A and 10B, the sensor temperature detecting period, which corresponds to the variation $\Delta T$ of the sensor temperature in the map 1, is preceded during the predetermined time ta after starting the engine during which the variation $\Delta T$ of the sensor temperature is relatively large. The greater the variation $\Delta T$ of the sensor temperature, the more the sensor temperature detecting frequency becomes, so that the sensor temperature may be detected by quickly following the changes of the sensor temperature.

Here, the variation of temperature of cooling water of the internal combustion engine may be used instead of the variation $\Delta T$ of the sensor temperature as the warming up condition in the map 1 in FIG. 9A. In this case, it is needless to say that the variation of the cooling water of the internal combustion engine is detected instead of the variation $\Delta T$ of the sensor temperature in Step 152 in FIG. 8. Further, either one of a variation $\Delta A/F$ of an air-fuel ratio A/F, a variation $\Delta Pm$ of a pressure of the intake pipe, variation $\Delta Ne$ of a number of rotation of the engine, variation $\Delta TAU$ of a fuel injection amount TAU, variation $\Delta TA$ of a throttle opening angle TA and variation $\Delta SPD$ of car speed SPD may be used instead of the variation of intake air amount Q as the variation of operation state in the map 2 in FIG. 9B. In this case, it is needless to say that either one of the variation $\Delta A/F$ of an air-fuel ratio A/F, the variation $\Delta Pm$ of the pressure of the intake pipe, variation $\Delta Ne$ of the number of rotation of the engine, variation $\Delta TAU$ of the fuel injection amount TAU, variation $\Delta TA$ of the throttle opening angle and variation $\Delta SPD$ of car speed is detected instead of the variation $\Delta Pm$ of the pressure of the intake pipe Pm in Step 154 in FIG. 8.

Figure 11:
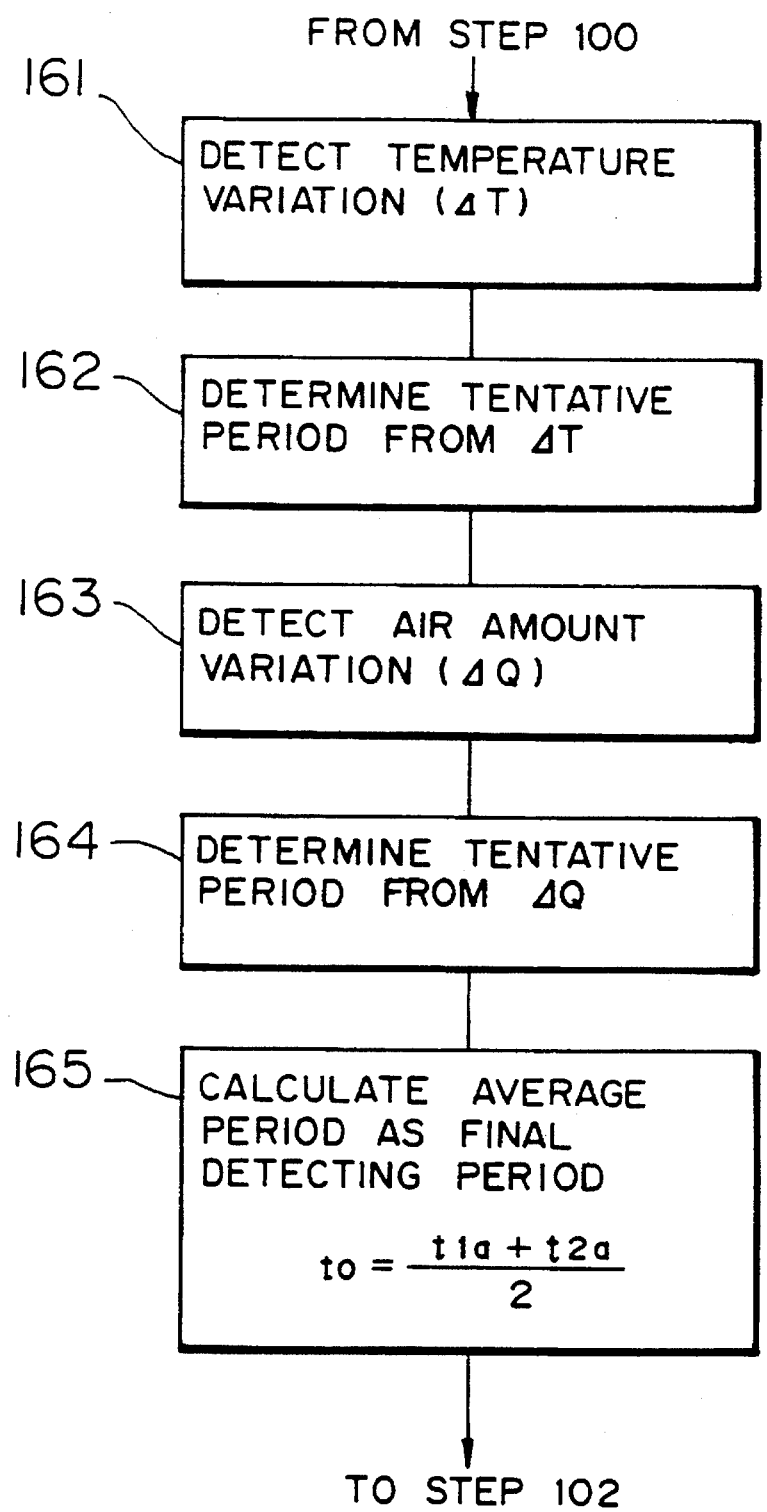
FIG. 11 is a flowchart showing a detail of a process for variably setting a temperature detecting period in each of the above-mentioned embodiments.

The modification of Step 101 for variably setting the temperature detecting period will be explained with reference to FIG. 11. At first, the variation $\Delta T$ of the sensor temperature of the oxygen sensor S is detected in Step 161 similarly to Step 152 in FIG. 8. Then, a tentative detecting period t1a is detected in Step 162 which is similar to Step 153 in FIG. 8, the variation $\Delta Q$ of the intake air amount Q is detected in Step 163 similar to Step 154 in FIG. 8, and a tentative detecting period t2a is detected in Step 164 similar to Step 155 in FIG. 8. Then, an average value of the tentative values t1a and t2a in Steps 162 and 164 is found in Step 165 to determine the final detecting period $t_0$. Thereby, the sensor temperature detecting period in which both the warming up condition and the changes of the engine state are always taken into account may be determined.

Figure 12:
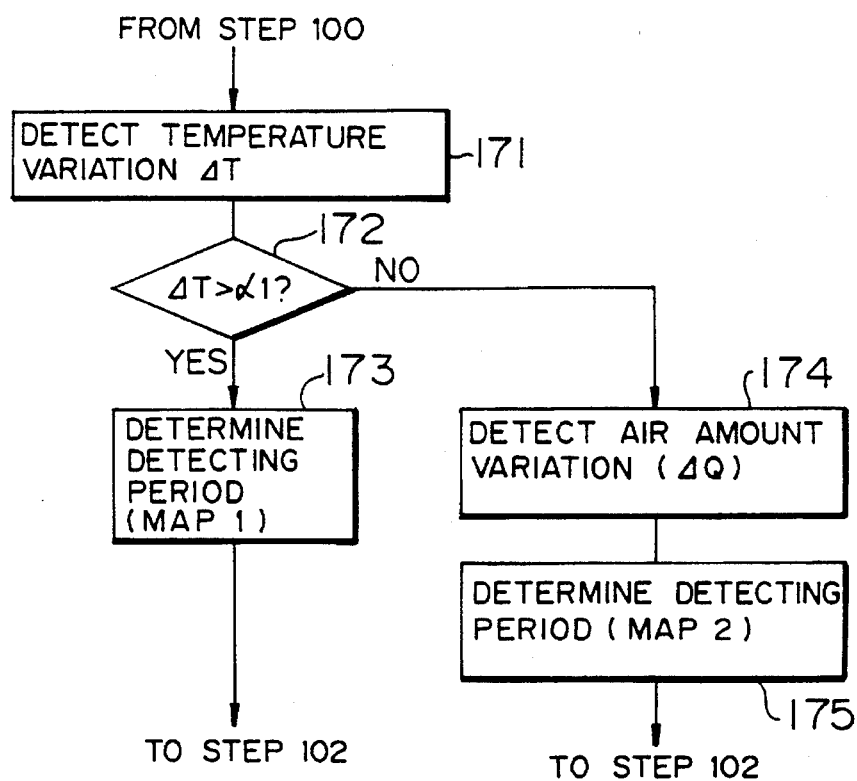
FIG. 12 is a flowchart showing a detail of a process for variably setting a temperature detecting period in each of the above-mentioned embodiments.

Further modification of Step 101 for variably setting the temperature detecting period will be explained with reference to FIG. 12. At first, the variation $\Delta T$ of the sensor temperature of the oxygen sensor S is detected in Step 171 similarly to Step 152 in FIG. 8 and it is determined in Step 172 whether the variation $\Delta T$ of the sensor temperature is more than a predetermined value $\alpha 1$ or not. If it is more than the predetermined value $\alpha 1$, the detecting period is determined in Step 173 similarly to Step 153 in FIG. 8. When the variation $\Delta T$ of the sensor temperature is less than the predetermined value, the variation $\Delta Q$ of the intake air amount Q of the internal combustion engine in Step 174 and the detecting period is determined in Step 175 similarly to Step 155 in FIG. 8.

Figure 13A:
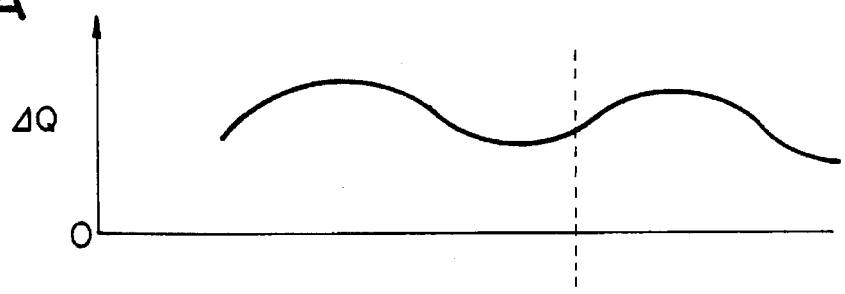
FIGS. 13A and 13B are time charts for explaining the operation of FIG. 12.
Figure 13B:
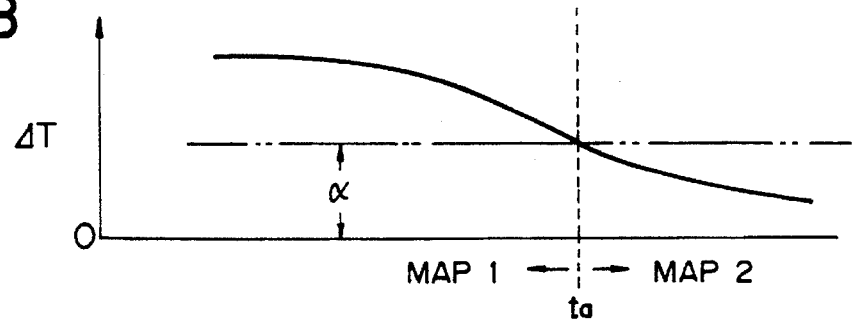

Thereby, as shown in FIGS. 13A and 13B, the sensor temperature detecting period which corresponds to the variation $\Delta T$ of the sensor temperature in the map 1 is preceded when the variation $\Delta T$ of the sensor temperature is greater than the predetermined value $\alpha$. The greater the variation $\Delta T$ of the sensor temperature, the more the sensor temperature detecting frequency increases, so that the sensor temperature may be detected by quickly following to the changes of the sensor temperature. When the variation $\Delta T$ of the sensor temperature becomes less than the predetermined value $\alpha$, the sensor temperature detecting period, which corresponds to the variation of the intake air amount Q in the map 2, is preceded. The greater the changes of the air-fuel ratio, the less the sensor temperature detecting frequency becomes, so that the air-fuel ratio may be detected quickly following to the changes of the air-fuel ratio.

Figure 14:
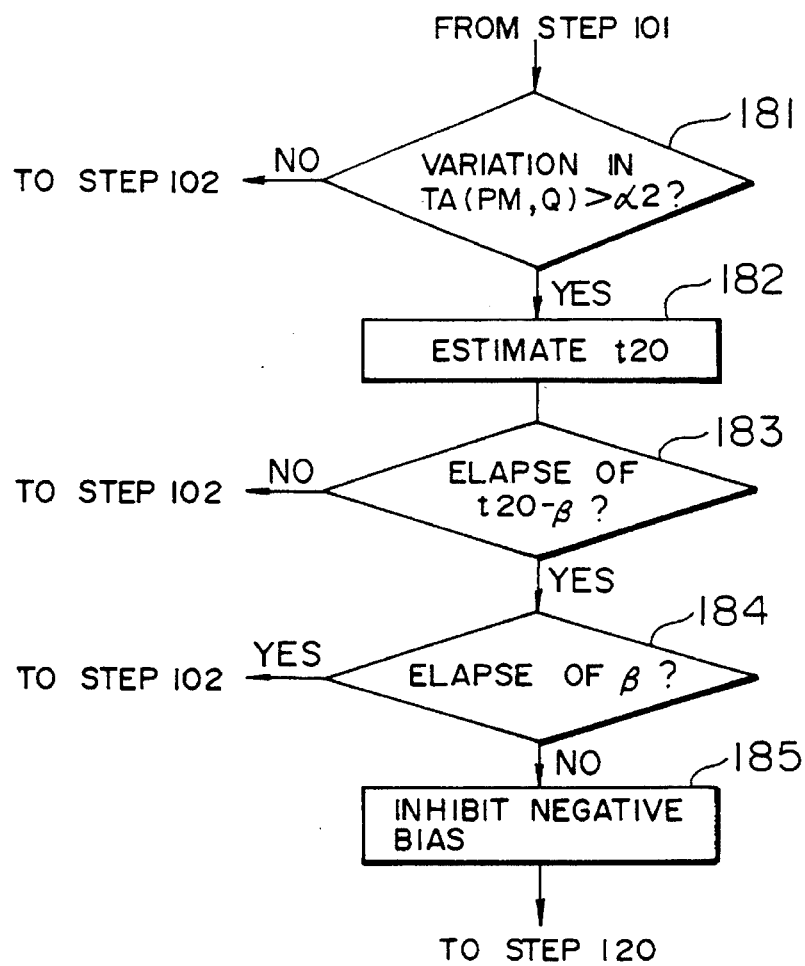
FIG. 14 is a flowchart, showing an additional embodiment to be added to FIG. 4, for inhibiting a negative bias when the air-fuel ratio changes.
Figure 15A:
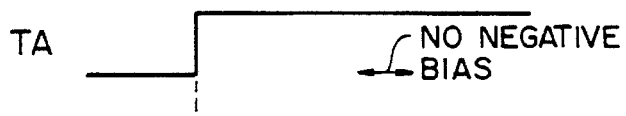
FIGS. 15A and 15B are time charts for explaining the operation of FIG. 14.
Figure 15B:
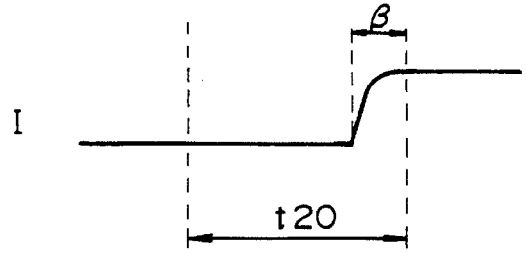

Modification of First and Second Embodiments: Inhibiting Negative Bias During Air-Fuel Ratio Changes Modification of the first and second embodiments for inhibiting to detect the sensor temperature of the oxygen sensor S and for causing the air-fuel ratio to be detected preferentially when the air-fuel ratio of the internal combustion engine is presumed to change rapidly will be explained with reference to FIGS. 14 and 15 hereinbelow. FIG. 14 shows a flowchart which is added after Step 101 in FIG. 4. It is determined in Step 181 whether the engine load, which is represented by at least one of the throttle opening angle TA, the pressure Pm of the intake pipe and the intake air amount Q of the internal combustion engine, fluctuates more than a predetermined value $\beta$ or not. When it is determined not to fluctuate more than the predetermined value $\alpha 2$, it is assumed that the air-fuel ratio does not rapidly change and the sensor temperature can be detected in Step 102 in FIG. 4. When the load is determined to fluctuate more than the predetermined value, it is assumed that the air-fuel ratio is rapidly changing and a stabilizing timing t20 from when the load, in particular the throttle opening angle, is changed to when the limiting current of the air-fuel ratio sensor S is stabilized and a change period $\beta$ from when the throttle opening angle is rapidly changed till when the limiting current of the air-fuel ratio sensor S is actually changed with a delay are estimated in Step 182 as shown in FIGS. 15A and 15B. Here, predetermined values of the stabilizing timing t20 and the change period $\beta$, which have been set beforehand by adaptive tests of the internal combustion engine, are stored in the ROM of the microcomputer 70. Although the stabilizing timing t20 and the change period $\beta$ may be fixed values, it is preferable to variably set the optimum values in response to engine parameters such as the variation and magnitude of the load.

It is determined in Step 183 whether a period (stabilizing timing t20–change period $\beta$) has passed or not. When it has not passed yet, it is assumed to be a response delayed period in which the limiting current of the air-fuel ratio sensor S has not changed yet since the throttle opening angle had been rapidly changed, allowing to detect the sensor temperature in Step 102 in FIG. 4. When the period (stabilizing timing t20–change period $\beta$) has passed, it is determined in Step 184 whether the change period $\beta$ has passed or not. When it is determined in Step 184 that the change period $\beta$ has passed, it is assumed that there is less fluctuation of the air-fuel ratio, allowing to detect the sensor temperature. When it is determined that the change period $\alpha$ has not passed yet, it is assumed that there is much fluctuation of the air-fuel ratio and the negative bias is inhibited to inhibit to detect the sensor temperature in Step 185. Then the air-fuel ratio is preferentially detected in Step 120.

According to this modification, the detection of the sensor temperature is inhibited only during the change period $\beta$ when the limiting current of the air-fuel ratio sensor S actually changes with the delay from when the throttle opening angle rapidly changed.

Further Modification of First and Second Embodiments: Inhibiting Negative Bias During Air-Fuel Ratio Changes The further modification for inhibiting to detect the sensor temperature of the oxygen sensor S and for causing the air-fuel ratio to be detected preferentially when the air-fuel ratio of the internal combustion engine is presumed to change rapidly will be explained with reference to FIGS. 16 and 17 hereinbelow. FIG. 16 shows a flowchart which is added after Step 101 in FIG. 4. As compared with the modification shown with reference to FIG. 14, the stabilizing timing t20 and a delay timing t21 from when the throttle opening angle TA has changed till when the actual air-fuel ratio at the position where the air-fuel ratio sensor S is disposed changes are estimated as shown in FIG. 17 by using Step 182*a*, instead of Step 182, it is determined whether the delay timing t21 has passed or not by using Step 183*a*, instead of Step 183, and it is determined whether a period (stabilizing timing t20–delay timing t21,) has passed or not by using Step 184*a*, instead of Step 184. Here, a predetermined value of the delay timing t21 which is set beforehand by the adaptive tests of the internal combustion engine, is also stored in the ROM of the microcomputer 70. Although the delay timing t21 may be a fixed value, it is preferable to variably set the optimum value in response to engine parameters such as the variation and magnitude of the load.

According to this embodiment, the negative bias is inhibited and the detection of the sensor temperature is inhibited during the period (stabilizing timing t20–delay timing t21) which is longer than that in the modification in FIG. 14, so that the detection of the air-fuel ratio is preceded for that period.

Figure 18:
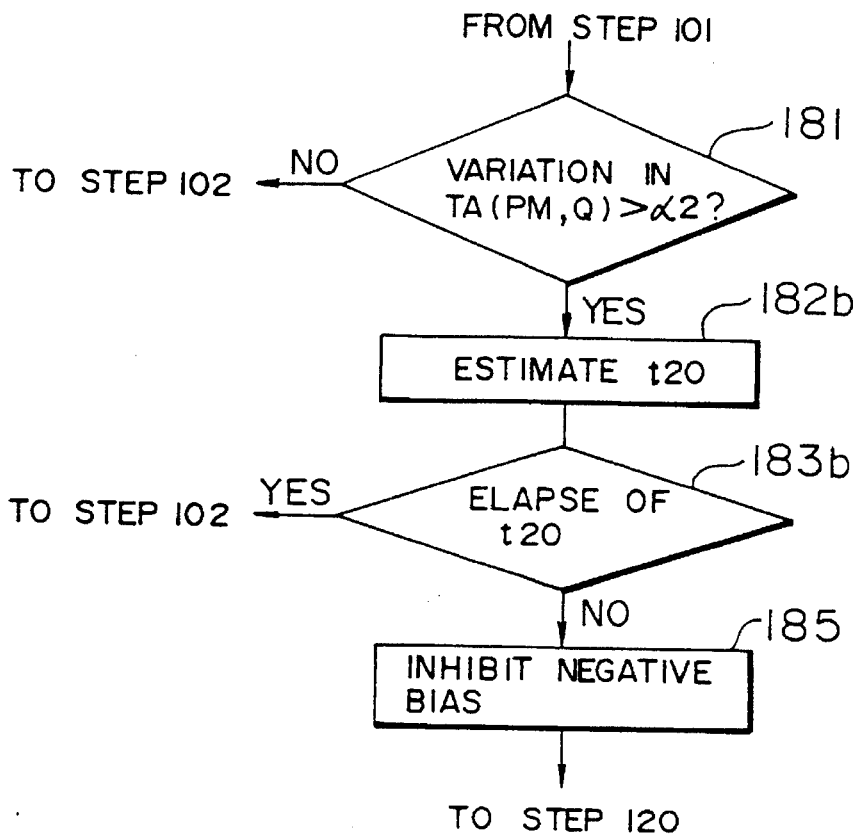
FIG. 18 is a flowchart, showing the additional embodiment to be added to FIG. 4, for inhibiting the negative bias when the air-fuel ratio changes.
Figure 19A:
FIGS. 19A and 19B are time charts for explaining the operation of FIG. 18.
Figure 19B:
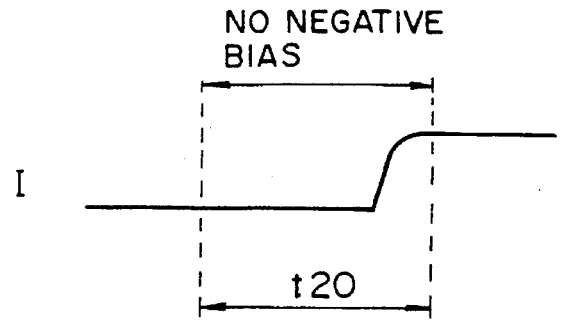

Still Further Modification of Embodiments: Inhibiting Negative Bias During Air-Fuel Ratio Changes The still further modification for inhibiting to detect the sensor temperature of the oxygen sensor S and for causing the air-fuel ratio to be detected preferentially when the air-fuel ratio of the internal combustion engine is presumed to change rapidly will be explained with reference to FIGS. 18 and 19 hereinbelow. FIG. 18 shows a flowchart which is added after Step 101 in FIG. 4. As compared with the modification shown with reference to FIG. 14, only the stabilizing timing t20 is estimated by using Step 182*b*, instead of Step 182 and it is determined whether the stabilizing timing t20 has passed or not since when the throttle opening angle TA changed as shown in FIGS. 19A and 19B by using Step 183*b*, instead of Steps 183 and 184. During this stabilizing timing t20, the negative bias is inhibited and the detection of the sensor temperature is inhibited.

Other Modifications

Although the timing varying means is structured by combining with the Step 101 for variably setting the temperature detecting period in the modifications for inhibiting the negative bias during when the air-fuel ratio changes rapidly, the timing varying means may be structured by applying the additional embodiments for inhibiting the negative bias during when the air-fuel ratio changes rapidly to what the positive bias and the negative bias are alternately executed per every certain period of time, without using Step 101 for variably setting the temperature detecting period.

Further, although the temperature detecting period is continuously changed on the basis of two maps before and after the air-fuel ratio becomes stable in the embodiments described above, it is possible to set only two periods so that the temperature detecting period after the stabilization becomes longer than that before the stabilization or to repeat the detection of the temperature and the detection of the air-fuel ratio with a fixed period after the oxygen sensor S is stabilized, without changing the temperature detecting period before and after the stabilization of the air-fuel ratio.

Still more, although the sensor section 20 is biased by the applied voltage V right after the elapse of the predetermined time t1 in the embodiments described above, the present invention is not confined only to that and it is possible to bias the sensor section 20 by the applied voltage V after the elapse of the predetermined time t1 and before the elapse of the predetermined time t11.

As described above, according to the first aspect of the present invention, there is an excellent effect that the time during which no oxygen concentration can be determined may be considerably shortened in the oxygen concentration detecting apparatus in the state where the temperature of the oxygen sensor changes less by allowing to prolong the time during which the positive voltage is applied to the oxygen sensor to determine the oxygen concentration by shortening the temperature detecting interval.

SECOND ASPECT

Next, a second aspect of the present invention will be explained with reference to FIG. 1B and FIGS. 20 through 22. For the second aspect, the same explanation with that of the aspect in FIGS. 2 through 19 is omitted and only their difference will be explained hereinbelow.

Figure 20:
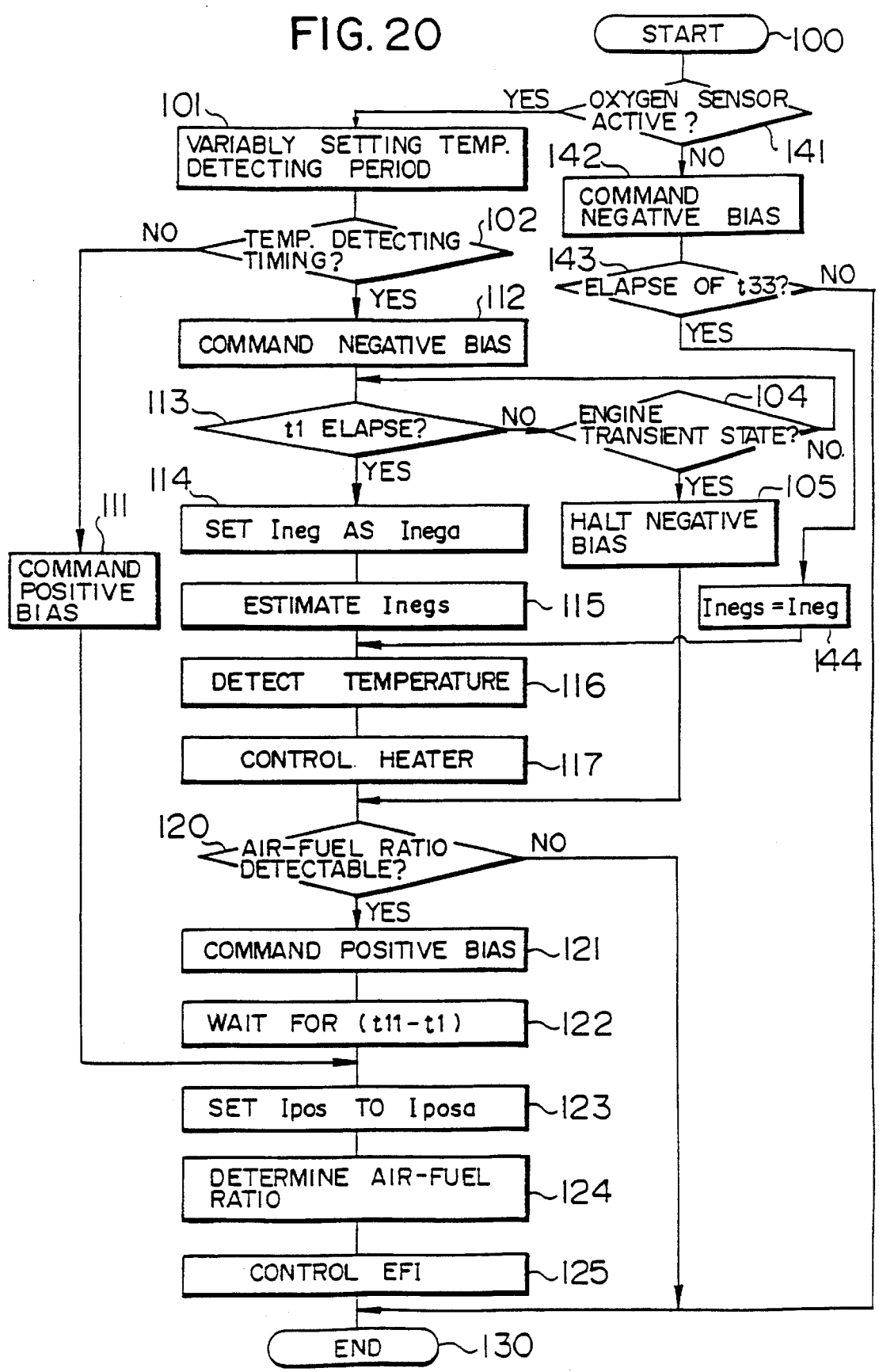
FIG. 20 is a flowchart showing the operation of the microcomputer according to an embodiment related to a second aspect of the present invention.

In the embodiment shown in FIG. 20, assume that the microcomputer 70 (FIG. 2) repeats the execution of the computer program after starting to execute the computer program at Step 100 following to a flowchart shown in FIG. 20 under the operation of the internal combustion engine 10. At first, it discriminates whether the oxygen sensor S is active or not in Step 141. The oxygen sensor S is determined to be active and is stable when either or both of the following discrimination conditions are met: 1) the sensor temperature of the oxygen sensor S has reached to a temperature sufficient to activate the oxygen sensor S; and 2) after the start of the internal combustion engine, a time tA sufficient to activate the oxygen sensor S has passed (here, although the time tA may be a fixed value, it is preferable to store and set in the ROM of the microcomputer 70 a value by which the lower the temperature of cooling water of the internal combustion engine, the longer the activation detecting time becomes). Then, it is determined to be "YES" in Step 141, the process is advanced to Step 101 and the totally same processes with those in FIG. 4 are carried out from Step 101 to Step 125.

On the other hand, at the time when the internal combustion engine has just started and when the oxygen sensor S is not activated yet, the microcomputer 70 determines to be "NO" in Step 141 and outputs a negative bias command necessary for applying a negative applied voltage Vneg to the sensor section 20 to the change-over switch circuit 43 of the bias control circuit 40 in Step 142. Then, in response to the negative bias command from the microcomputer 70, the change-over switch circuit 43 is put into the second change-over state and connects the negative side electrode of the DC power source 42 to the input terminal 51 of the current detecting circuit 50. Thereby, the current Ineg (see the solid line shown in FIG. 21A) from the DC power source 42 starts to flow through the lead wire 41a, the exhaust gas side electrode layer 23, the solid electrolyte layer 22, the atmosphere side electrode layer 24 of the sensor section 20, the lead wire 42a and the current detecting circuit 50.

Figure 21A:
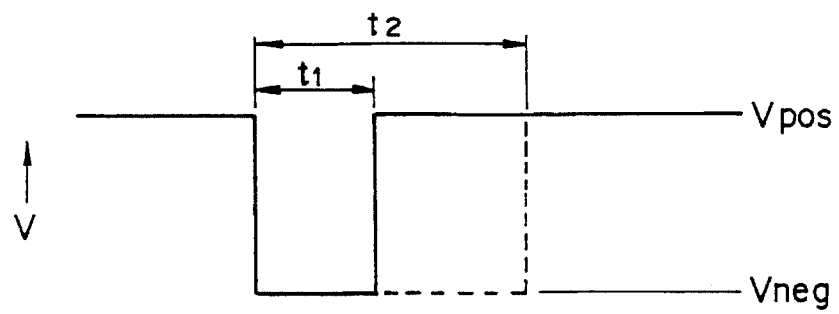
FIGS. 21A and 21B are time charts showing waveforms of voltages applied to the sensor section and waveforms of currents flowing through the sensor section when negatively and positively biased.
Figure 21B:
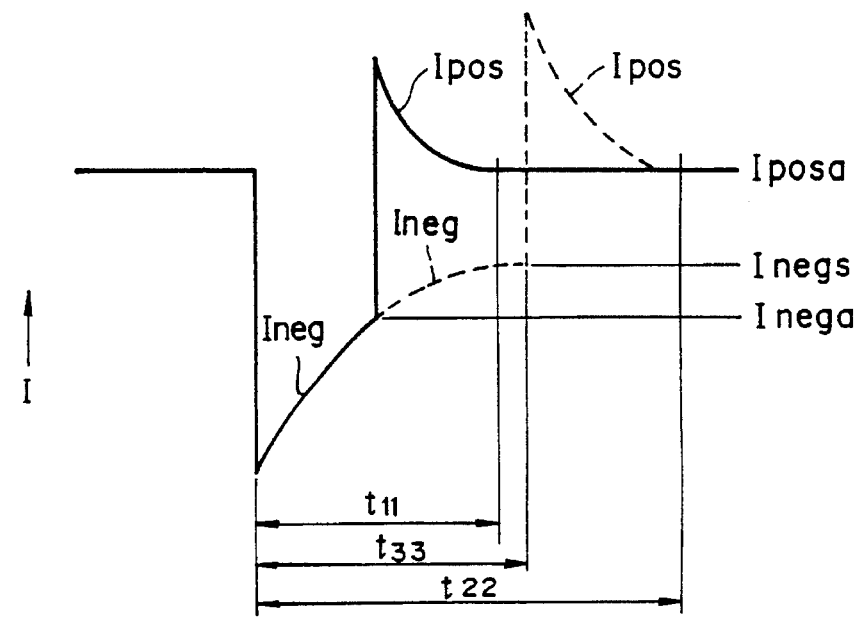

After the arithmetic operation described above, the microcomputer 70 determines whether a predetermined time t33 has passed or not to wait for the predetermined time t33 in Step 143. Here, the predetermined time t33 is set at the time when the current Ineg saturates from when the negative bias is applied to the sensor section 20 (FIG. 21). When the predetermined time t33 has not passed yet, the microcomputer 70 assumes that the current Ineg has not saturated yet and advances the process to Step 130 to end. When the microcomputer 70 determines in Step 143 that the predetermined time t33 has passed, it advances the process to Step 144 and then to Step 116 after setting the current Ineg detected at that as the saturated current Inegs.

Figure 22A:
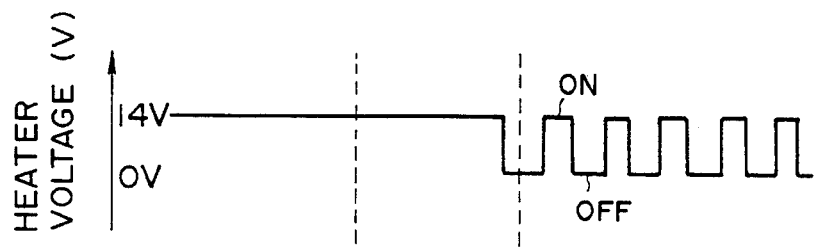
FIGS. 22A through 22C are time charts for explaining the operation of the embodiment of FIG. 20.
Figure 22B:
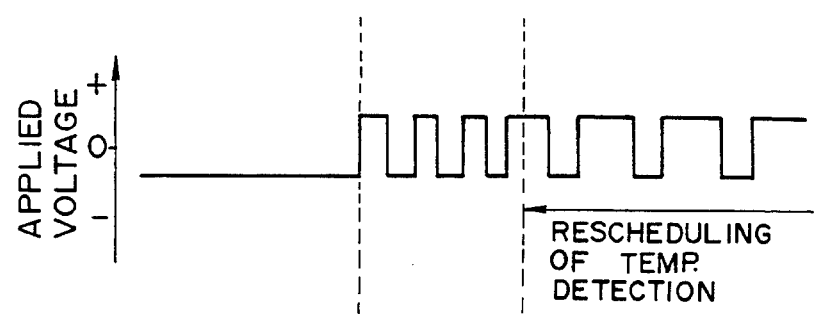
Figure 22C:
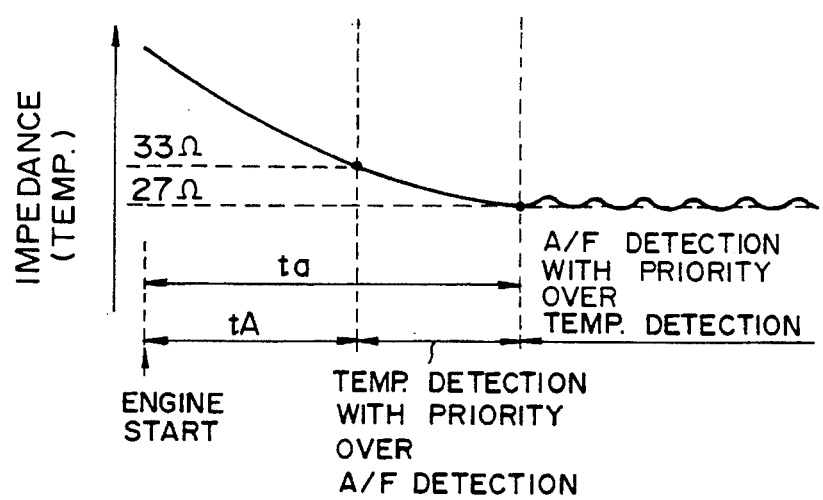
Figure 23:
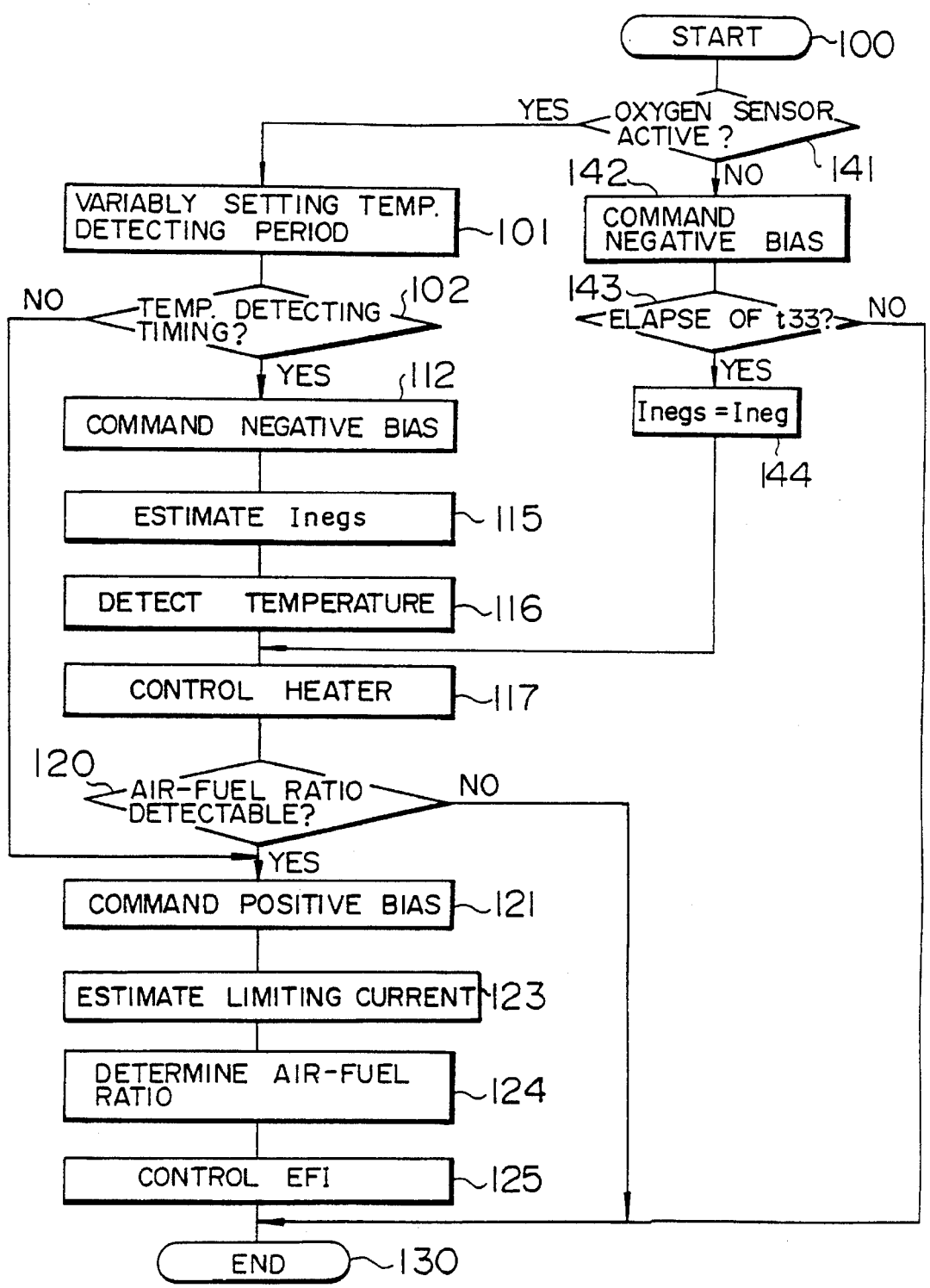
FIG. 23 is a flowchart of an embodiment related to a third aspect of the present invention.

Thereby, when the oxygen sensor S has not been activated yet, the sensor temperature of the oxygen sensor S is continuously detected on the basis of the saturation current Ineg (no positive voltage is applied to the sensor section 20 and hence no air-fuel ratio is detected) by going through Step 116, Step 117, Step 120 and Step 130 and repeating Step 141, Step 142, Step 143, Step 144 and so on. Thereby, as shown in FIG. 22C, the sensor temperature may be quickly raised to the activation temperature by controlling the heating of the heater 26 on the basis of the sensor temperature continuously detected, so that the measurement of the accurate oxygen concentration may be started in a short time after the start of the internal combustion engine.

Note that it is preferable to set the initial value of the sensor temperature of the oxygen sensor S when the internal combustion engine is started at a low temperature when the oxygen sensor S is inactive, e.g. at a value equal to that of the engine cooling water when the engine is started, considering a case when the oxygen sensor S is determined to be active when the sensor temperature of the oxygen sensor S is more than the predetermined value in Step 141.

As described above, according to the second aspect of the present invention, there is an excellent effect that because the sensor temperature of the oxygen sensor is continuously detected until the oxygen sensor is activated after the start of the engine and the sensor temperature may be raised to the activation temperature quickly by controlling the heating of the heater on the basis of the detected temperature, the accurate oxygen concentration may be measured in a short time after the start of the engine.

THIRD ASPECT

Next, a third aspect of the present invention will be explained in terms of a difference from the second aspect with reference to FIG. 1C and FIGS. 23 through 27. The microcomputer 70 (FIG. 2) executes a computer program following a flowchart shown in FIG. 23 under the operation of the internal combustion engine 10. This flowchart corresponds to what the Steps 104, 105, 111, 113, 114 and 122 are eliminated from the flowchart in FIG. 20 and the content of processing of Step 123 is modified.

Figure 24A:
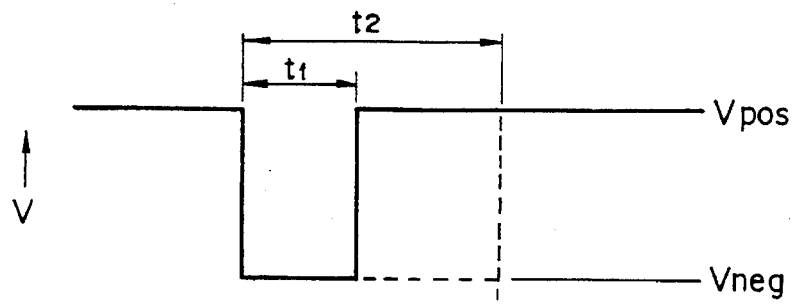
FIGS. 24A and 24B are time charts showing waveforms of voltages applied to the sensor section and waveforms of currents flowing through the sensor section when negatively and positively biased.

The microcomputer 70 determines to be "YES" in Step 102 based on the determination of the temperature detecting period set in Step 101 and outputs a negative bias command necessary for applying a negative applied voltage Vneg to the sensor section 20 to the change-over switch circuit 43 of the bias control circuit 40 (FIG. 24A). Then, in response to the negative bias command from the microcomputer 70, the change-over switch circuit 43 is put into the second change-over state and connects the negative side electrode of the DC power source 42 to the input terminal 51 of the current detecting circuit 50. Thereby, the current Ineg (see the solid line in FIG. 24A) from the DC power source 42 starts to flow through the lead wire 41a, the exhaust gas side electrode layer 23, the solid electrolyte layer 22, the atmosphere side electrode layer 24 of the sensor section 20, the lead wire 42a and the current detecting circuit 50.

After the arithmetic operation in Step 112 described above, the microcomputer 70 sets the current Inega from the converted current Ineg from the A-D converter 60 and estimates the saturation current Inegs in response to the current Inega and on the basis of the transient phenomenon equation representing the relationship between the current Ineg and the applied voltage Vneg in Step 115. The transient phenomenon equation is formed of the time when the sensor section 20 is negatively biased as the initial condition and is stored in the ROM of the microcomputer 70 beforehand. After that, the microcomputer 70 detects the temperature of the sensor section 20 in Step 116 on the basis of the estimated saturation current-temperature characteristic data in response to the estimated saturation current Inegs. The estimated saturation current-temperature characteristic data is stored in the ROM of the microcomputer 70 beforehand as data representing the direct proportional relationship between the estimated saturation current |Inegs| and the temperature of the sensor section 20.

When the temperature of the sensor section 20 is thus detected, the microcomputer 70 implements an arithmetic operation in Step 117 to heat and control the heater 26 so as to raise and maintain the temperature detected in Step 116 to a temperature T1 (characteristic line L1). Then, the heating control circuit 80 heats and controls the heater 26 on the basis of the heating control arithmetic operation implemented by the microcomputer 70. Thereby, even if the temperature of the sensor section 20 drops temporarily, it is returned to the temperature T1 quickly.

Due to that, judging that the air-fuel ratio may be stably detected, the microcomputer 70 determines to be "YES" in Step 120 and advances the computer program to Step 121. Then, the microcomputer 70 outputs to the bias control circuit 40 a positive bias command which is necessary for applying the positive applied voltage Vpos to the sensor section 20. Then, the bias control circuit 40 applies the applied voltage Vpos from the DC power source 41 to the sensor section 20 similarly to the case described above. It means that the applied voltage Vpos is applied to the sensor section 20 right after an elapse of the above-mentioned predetermined period t1. Thereby, the current Ipos from the DC power source 41 starts to flow through the lead wire 41a, the exhaust gas side electrode layer 23, the solid electrolyte layer 22, the atmosphere side electrode layer 24 of the sensor section 20, the lead wire 42a and the current detecting circuit 50 as a limiting current. In other words, as shown in FIG. 24B, the current Ineg flowing through the sensor section 20 is inverted and rises to become the current Ipos right after the elapse of the predetermined period T1 and then starts to exponentially decrease thereafter as shown by the solid line in the figure.

Figure 7:
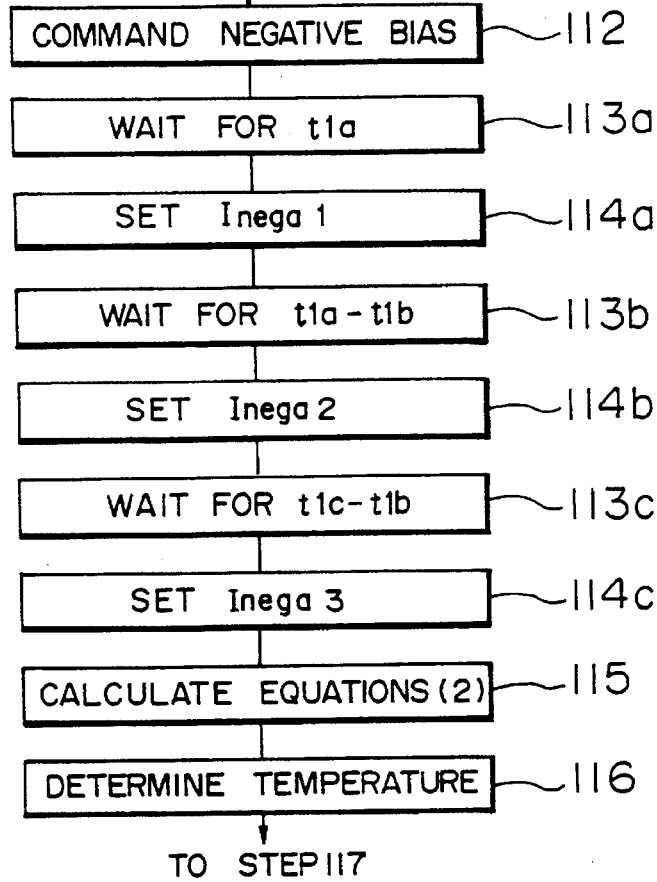
FIG. 7 is a flowchart showing the operation of the microcomputer in another embodiment related to the first aspect.
Figure 8:
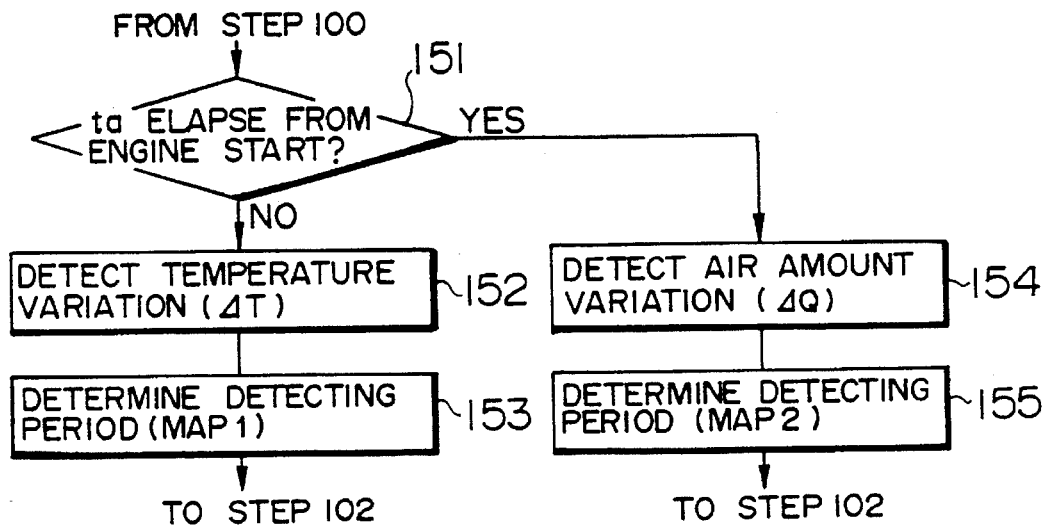
FIG. 8 is a flowchart showing a detail of a process for variably setting the temperature detecting period in each of the above-mentioned embodiments.

It should be noted that Step 115 for estimating the saturation current is characterized in that the saturation current Inegs of the current Ineg is estimated by measuring the value Inega at one time in the process of increase of the current Ineg three times, similarly to the aspect shown with reference to FIG. 7. Thus, the saturation current Inegs may be estimated more accurately.

Figure 24B:
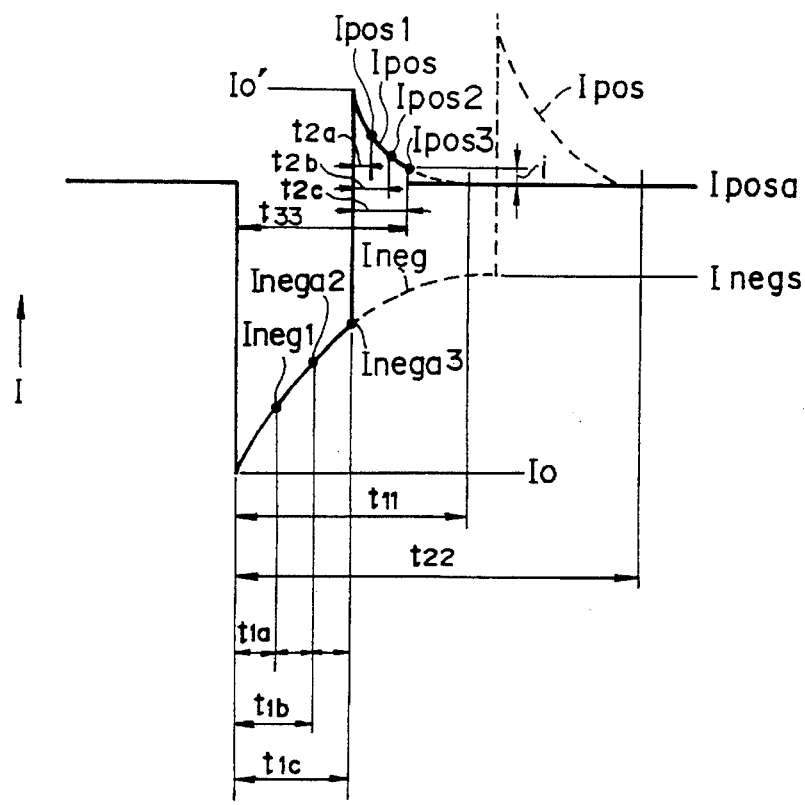

FIGS. 24A and 24B shows voltages V applied to the sensor section 20 and currents I flowing through the sensor section 20 at that time. In FIG. 24B, a current Ineg which flows when the applied voltage V, is changed over from Vpos to Vneg changes exponentially as expressed by the equation (1) wherein ($I_0$) represents a peak current value, (Ineg) a saturated current value (converged current value) and (T) a time constant.

Next, the detail of Step 123 for estimating a limiting current which follows Step 121 will be explained with reference to FIG. 25. This embodiment is characterized in that the limiting current Iposa of the current Ipos is estimated by measuring the value Ipos at one time in the process of decrease of the current Ipos three times. Thus, the limiting current Iposa may be estimated more accurately.

In FIG. 24B, a current Ipos, which flows when the applied voltage V is changed over from Vneg to Vpos, changes exponentially as expressed by the following equation 4 wherein ($I_0'$) represents a peak current value, (Iposa) a limiting current value (converged limiting current value) and (T) a time constant.

$$Ipos=Iposa+(I_0'-Iposa)e^{-t/T} \qquad (4)$$

When the peak current value $I_0'$, limiting current value (converged limiting current value) Iposa and time constant T are unknown, it is necessary to detect current values at three points on the Ipos curve Ipos1, Ipos2 and Ipos3 in order to find Iposa. Then, Iposa is found by obtaining a solution of the following simultaneous equations from the current values detected at the three points:

$$Ipos1=Iposa+(I_0'-Iposa)e^{-t2a/T}$$
$$Ipos2=Iposa+(I_0'-Iposa)e^{-t2b/T} \qquad (5)$$
$$Ipos3=Iposa+(I_0'-Iposa)e^{-t2c/T}$$

Here, Ipos1, Ipos2 and Ipos3 are values of the current value Ipos after times t2a, t2b and t2c from when the applied voltage V is changed over from Vneg to Vpos.

For example, when it is assumed as t2a=0 and t2b=t2c−t2b to simplify the calculation and when those values are substituted for Equation 5, Iposa can be found by the following Equation 6:

$$Iposa=(Iposa2^2-Ipos3*Ipos1)/(2\ Ipos2-Ipos3-Ipos1) \qquad (6)$$

Next, the operation of this embodiment will be explained with reference to a flowchart in FIG. 25.

After the arithmetic operation in Step 121, the microcomputer 70 determines in Step 122a whether the predetermined time t11 (which is set as negative bias time t1+predetermined time sufficient for the detected current to converge since when the positive bias voltage is applied) has passed since when the negative bias voltage was applied to the sensor section 20 or the predetermined time t11−t1 has passed since when the positive bias voltage was applied waits for the predetermined time t1a at Step 113a. If the answer is "YES", it sets the converted current Ipos from the A-D converter 60 as the limiting current Iposa as it is in Step 122b, assuming that the detected current has converged. When the answer is "NO" in Step 122a, the process is advanced to Step 123a and thereafter to estimate the limiting current after the convergence from the detected currents on the way of the convergence.

That is, the microcomputer 70 waits for the predetermined time t2a in Step 123a. Ending to wait for the time in Step 123a, the microcomputer 70 detects the current value and sets the converted current Ipos from the A-D converter 60 as the current Ipos1 in Step 123b. After that, the microcomputer 70 waits for the predetermined time t2b−t2a in Step 123c. Ending to wait for the time in Step 123c, the microcomputer 70 detects the current value and sets the converted current Ipos from the A-D converter 60 as the current Ipos2 in Step 123d. Next, the microcomputer 70 waits for the predetermined time t2c−t2b in Step 123e.

Ending to wait for the time in Step 123e, the microcomputer 70 detects the current value and sets the converted current from the A-D converter 60 as the current Ipos3 in Step 123f. After that, the microcomputer 70 calculates the saturation limiting current Iposa based on the simultaneous equations (5) described above in Step 123g. The simultaneous equations (5) are formed of the time when the positive bias is applied as the initial condition and is stored in the ROM of the microcomputer 70 beforehand. After that, the microcomputer 70 sets the saturated limiting current Iposa estimated in Step 123f as the limiting current Iposa in Step 122c. Then, the microcomputer 70 determines the oxygen concentration, i.e. the air-fuel ratio, in Step 124 in response to the limiting current Iposa set in Step 122b or 122c based on the oxygen concentration-limiting current data shown in FIG. 5.

As described above, the embodiment shown in FIG. 25 is characterized in that the limiting current Iposa of the current Ipos is estimated by measuring the value of one time in the process of the decrease of the current Ipos three times and that thereby the limiting current Iposa can be estimated more accurately.

Further, because the oxygen concentration, i.e. the air-fuel ratio, is continuously detected by repeatedly setting the detected current after the convergence as the limiting current as it is during when the positive bias is applied after when the positive bias voltage has been applied to the sensor section 20 and after when the time sufficient for the detected current to converge has elapsed, the oxygen concentration may be accurately detected repeatedly in response to the changes of the oxygen concentration after when the detected current has converged.

Further, the sensor section 20 is positively biased by the applied voltage Vpos right after the elapse of the predetermined time t1 and the air-fuel ratio is detected at the time of t33 on the way of the convergence before the predetermined time (t11–t1) elapses, which is the convergence period in which the current Ipos flowing through the sensor section 20 due to the positive bias ends to decrease by the currents Ipos1 through Ipos3 until that time, the air-fuel ratio can be quickly detected as compared with the prior art. Here, the leading edge peak level of the current Ipos in the case of the present embodiment is maintained relatively low as compared with the leading edge peak level of the current Ipos in the prior art case and the current Ipos in the present embodiment rapidly decreases as compared with the current Ipos in the prior art as described above, so that the air-fuel ratio can be quickly detected further.

Note that although the sensor section 20 is positively biased by the applied voltage Vpos right after the elapse of the predetermined time t1 in the embodiment described above, the present invention is not confined only to that and it is possible to positively bias the sensor section 20 by the applied voltage Vpos after the elapse of the predetermined time t1 and before the elapse of the predetermined time t11.

Next, modification of Step 123 for estimating limiting current will be explained with reference to FIG. 26. In this modification, as compared with the embodiment shown in FIG. 25, Step 122a is omitted and instead of that, Step 122d is added after Step 123g. When it is determined in Step 122d that the previous value and the present value of the detected current Ipos are almost equal, the detected current is assumed to have converged and the present detected current after the convergence is set as the limiting current as it is in Step 122b. When the previous value and the present value of the detected current Ipos are determined not to be equal in Step 122d, the detected current is assumed to be on the way of convergence and the value estimated in Step 123g is set as the limiting current in Step 122c. The present embodiment also allows to obtain the same effect with that in FIG. 25.

Figure 25:
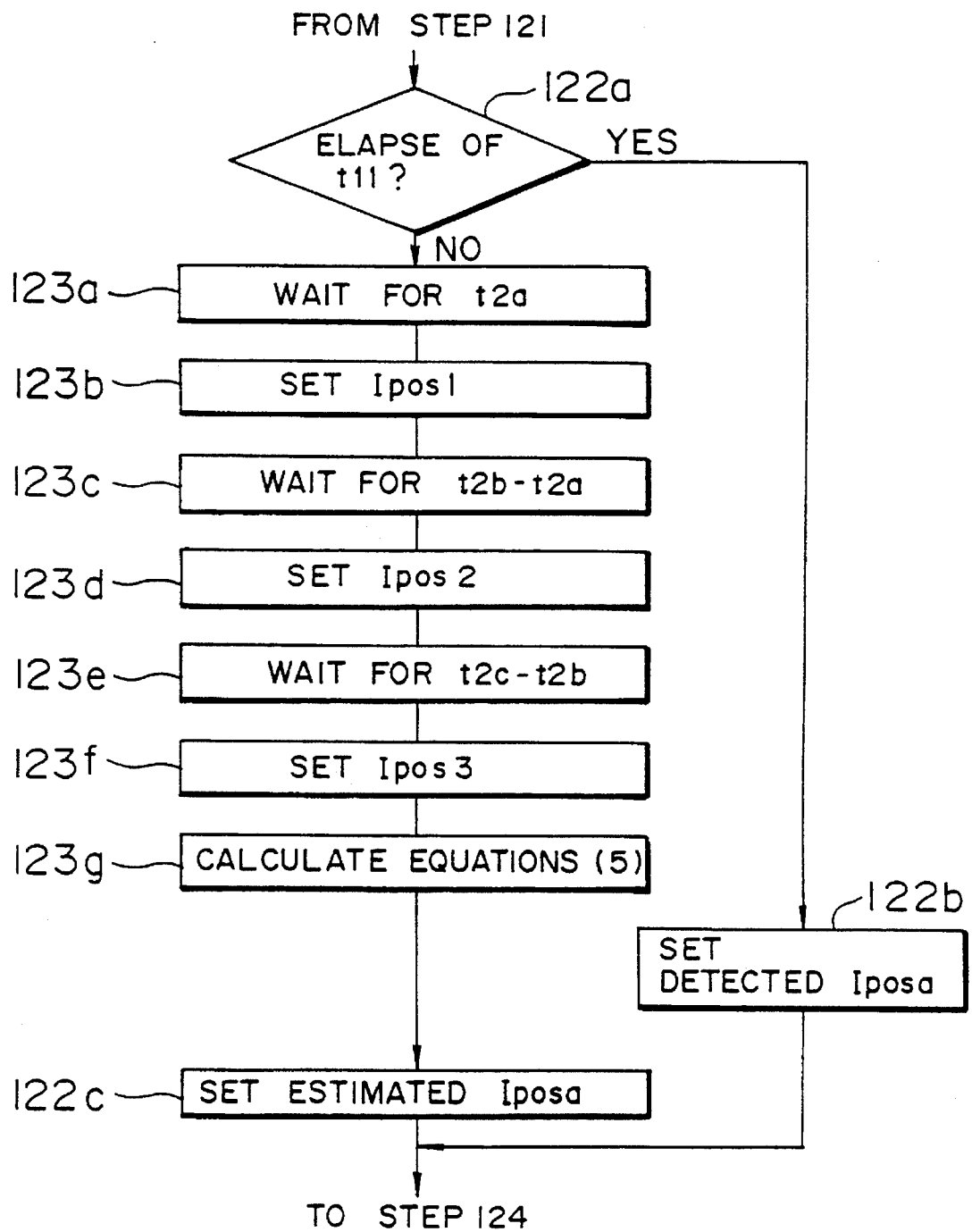
FIG. 25 is a flowchart showing a detail of a process for estimating the limiting current in the above-mentioned embodiments.
Figure 26:
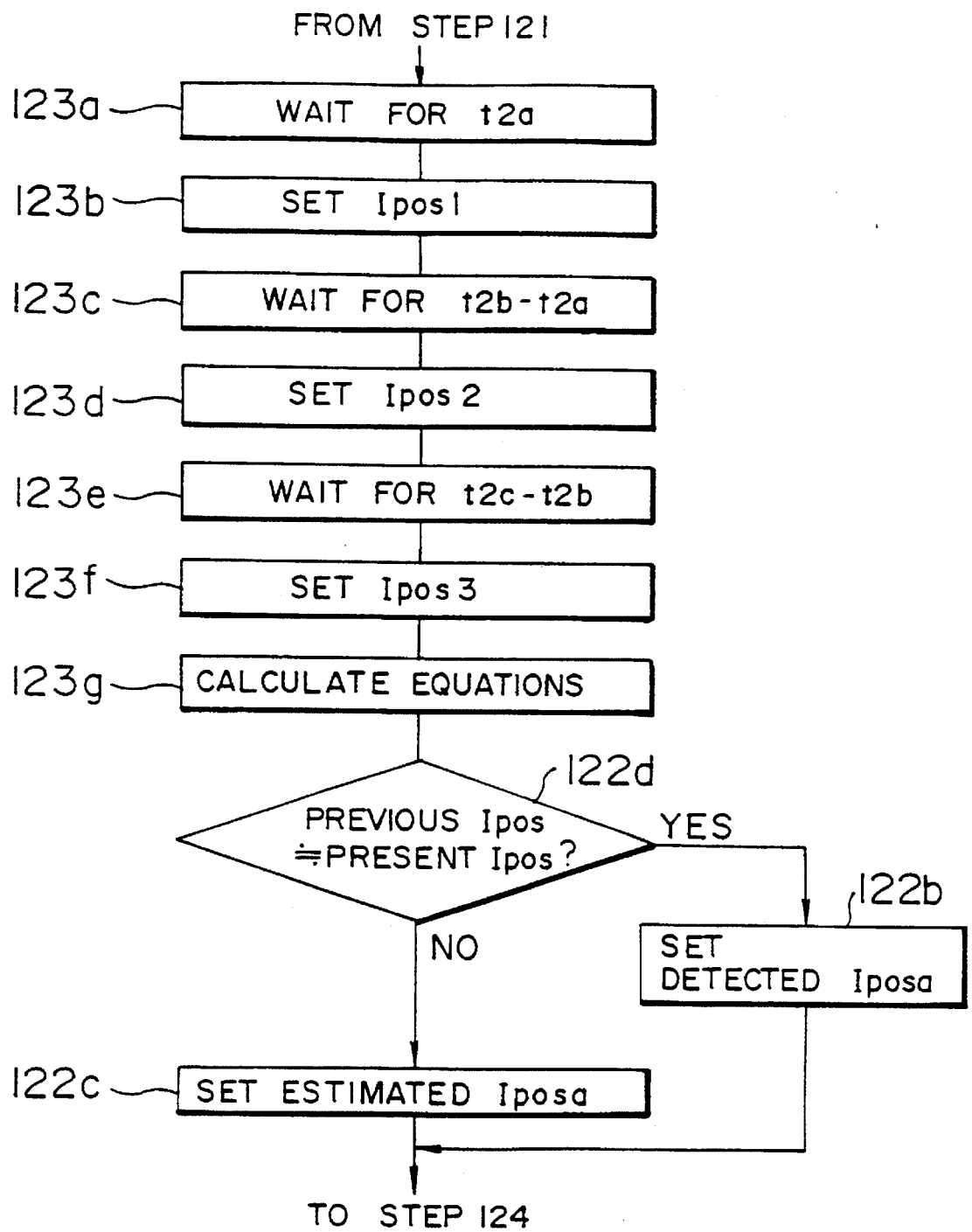
FIG. 26 is a flowchart showing another detail of the process for estimating the limiting current in the above-mentioned embodiments.
Figure 27:
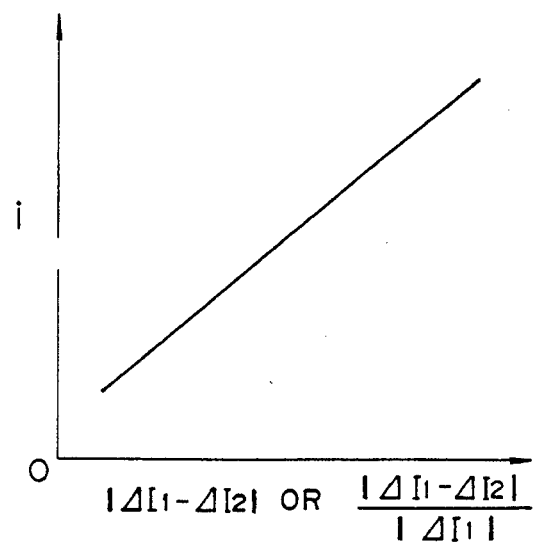
FIG. 27 is a graph showing a map of deviation i of a limiting current to a variation of the absolute value of a detected current.

Although the limiting current Iposa is found from the solution of Equation 5 in Step 123g in FIGS. 25 and 26 in the embodiment related to the third aspect of the present invention, it is possible to find the saturation current Inegs and limiting current I from the maps in the ROM from a variation of absolute value of the detected current. Now a case of finding the limiting current Iposa by the map will be described. At first, (Ipos1–Ipos2)–$\Delta$I1 and (IPos2–Ipos3)= $\Delta$I2 are found. From that result, a variation of absolute value (rate of change) of $|\Delta I1-\Delta I2|$ or $(|\Delta I1-\Delta I2|)/|\Delta I1|$ is found and a deviation i from Iposa2 to Iposa (FIG. 24) is found on the basis of a characteristic of $|\Delta I1-\Delta I2|$ or $(|\Delta I1-\Delta I2|)/|\Delta I1|$ and the deviation i (set so that the greater the variation of absolute value, the larger the deviation i becomes) stored in the ROM by means of the map beforehand and the limiting current Iposa is found from a calculation of Iposa=Ipos3–i. Thereby, the limiting current Iposa may be estimated accurately without calculating complicated equations even if the gradient of the convergence of the detected current is not defined to be one. If the gradient of the convergence of the detected current is defined to be one, the limiting current Iposa may be found by calculating Iposa=Ipos2–i by finding the deviation i on the basis of the characteristic of deviation i from Ipos2 to Iposa to $\Delta$I1 from the map in the ROM by using only the variation of absolute value of (Ipos1–Ipos2)= $\Delta$I1.

Although the limiting current Iposa is repeatedly detected until the next temperature detecting timing even after the convergence of the detected current in the embodiment described above, it is possible not to detect the limiting current Iposa after the convergence by always estimating the limiting current Iposa by the detected current on the way of the convergence by applying alternating voltage of negative and positive biases to the sensor section 20 with a constant frequency of t33 in FIGS. 24A and 24B. At this time, although Steps 122a and 122b in FIG. 8 and Steps 122d and 122b in FIG. 9 may be omitted, no limiting current Iposa is detected by the detected current after the convergence at all and the limiting current Iposa is estimated only by the detected current on the way of the convergence, so that a deviation between the estimated limiting current and the actual limiting current after the convergence cannot be taken into account even if it is present.

As described above, according to the third aspect of the present invention, there is an excellent effect that because the limiting current after the convergence is estimated from the detected current on the way of the convergence since when the positive voltage has been applied and the oxygen concentration is determined on the basis of the estimated limiting current, the time since the application of the positive voltage till when the oxygen concentration is determined may be shortened and the time during which no oxygen concentration can be determined may be considerably shortened.

Figure 28:
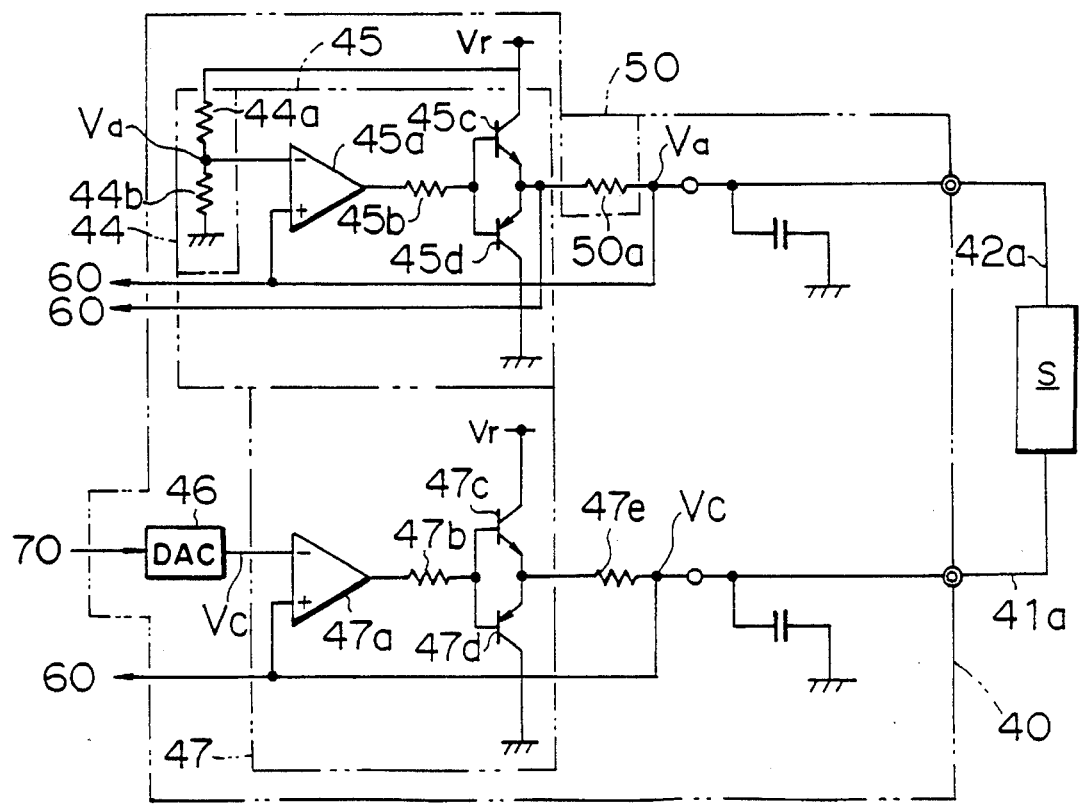
FIG. 28 is an electrical connection diagram showing a bias control circuit shown in FIG. 2.

FIG. 28 shows a detailed structure of the electrical circuit of the part of the bias control circuit 40 shown in FIG. 2. A reference voltage circuit 44 divides a constant voltage Vr by each of voltage dividing resistors 44a and 44b to produce a constant reference voltage Va. A first voltage supplying circuit 45 supplies the same voltage Va which is equal to the constant voltage Va of the reference voltage circuit 44 to one terminal of the oxygen sensor S (lead wire 42a connected to the atmosphere gas side electrode layer 24) and comprises an operational amplifier 45a whose negative side input terminal is connected to a dividing point of the voltage dividing resistors and whose positive side input terminal is connected to one terminal of the oxygen sensor S, a resistor 45b whose one end is connected to an output terminal of the operational amplifier 45a and NPN transistor 45c and PNP transistor 45d whose bases are connected to the other end of the resistor 45b. A collector of the NPN transistor 45c is connected to the constant voltage Vr and an emitter thereof is connected to one terminal of the oxygen sensor S via a current detecting resistor 50a which composes the current detecting circuit 50. An emitter of the PNP transistor 45d is connected to the emitter of the NPN transistor 45c and a collector thereof is grounded.

A D-A converter 46 converts a bias command signal (digital signal) from the microcomputer 70 into an analog signal voltage Vc. A second voltage supplying circuit 47 supplies a voltage Vc equal to the output voltage Vc of the D-A converter 46 to the other terminal (lead wire 41a connected to the exhaust gas side electrode layer 23) of the oxygen sensor S and comprises an operational amplifier 47a whose negative side input terminal is connected to an output of the D-A converter 46 and whose positive side input terminal is connected to the other terminal of the oxygen sensor S, a resistor 47b whose one end is connected to an output terminal of the operational amplifier 47a, and an NPN transistor 47c and PNP transistor 47d whose bases are connected to the other end of the resistor 47b. A collector of the NPN transistor 47c is connected to the constant voltage Vr and an emitter thereof is connected to the other terminal of the oxygen sensor S via a resistor 47e. An emitter of the PNP transistor 47d is connected to the emitter of the NPN transistor 47c and a collector thereof is grounded.

Thereby, the constant voltage Va is always supplied to one terminal of the oxygen sensor S. When the bias command signal which corresponds to a voltage higher than the constant voltage Va is supplied from the microcomputer 70 to the D-A converter 46, the voltage Vc which is lower than the constant voltage Va is supplied to the other terminal of the oxygen sensor S and the oxygen sensor S is positively biased by the voltage of Va–Vc (Va>Vc). When the bias command signal, which corresponds to a voltage lower than the constant voltage Va, is supplied from the microcomputer 70 to the D-A converter 46, the voltage Vc which is higher than the constant voltage Va is supplied to the other terminal of the oxygen sensor S and the oxygen sensor S is negatively biased by the voltage of Va–Vc (Va>Vc). Thus, the bias voltage of the oxygen sensor S may be controlled to either a positive or negative value arbitrarily on the basis of the bias command supplied from the microcomputer 70 to the D-A converter 46.

Then, a difference of voltages (Vb–Va) at both ends of the current detecting resistor 50a is input as a detected current from the current detecting circuit 50 to the A-D converter 60 and a difference of voltages (Va–Vc) at both ends of the oxygen sensor S is input as an induced voltage of the oxygen sensor S to the A-D converter 60.

It is to be noted that the essential feature of the present invention resides in the varying the voltage switching timing. Therefore, detection of the saturation current for detecting the oxygen concentration and the element temperature is not limited to estimation of the saturation current from the detection current in the course of convergence as in the third aspect, but the current may be detected after the saturation as disclosed in U.S. Pat. Nos. 4,543,176 or 4,626,338. Further, the element temperature may be detected as disclosed in U.S. Pat. No. 4,882,030. Still further, the voltage applied to the oxygen sensor S for detecting the element temperature is not limited to the negative voltage, but it may be another voltage different from the one applied to detect the limiting current.

The present invention having been described should not be restricted to the disclosed embodiments but may be modified in many other ways without departing from the spirit of the invention.

What is claimed is:

1. An oxygen concentration detecting apparatus comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of each of said voltages;

impedance detecting means for detecting a DC impedance of said oxygen sensor based on said current detected during application of said negative voltage to said oxygen sensor for said set period of time;

oxygen concentration detecting means for detecting an oxygen concentration based on said current detected during application of said positive voltage to said oxygen sensor; and timing varying means for variably setting a timing for changing over said voltage applying means to apply said negative voltage to said oxygen sensor, wherein said timing varying means includes means for changing said timing to change over said voltage applying means to provide said negative voltage in response to said DC impedance detected by said impedance detecting means, said change over occurring more frequently as said DC impedance increases.

2. An apparatus according to claim 1, wherein:

said timing varying means includes means for changing said timing for changing over to said negative voltage in response to said oxygen concentration detected by said oxygen concentration detecting means.

3. An apparatus according to claim 1, further comprising:

operation state detecting means for detecting an operation state of an internal combustion engine; and said timing varying means including means for changing said timing for changing over said negative voltage in response to said operation state detected by said operation state detecting means.

4. An apparatus according to claim 3, wherein:

said operation state detecting means includes transient operation detecting means for detecting a transient operation state of said internal combustion engine; and said timing varying means controlling timing for changing over said negative voltage is set so that said set period of time is prolonged if said transient operation state is detected by said transient operation detecting means.

5. An apparatus according to claim 3, wherein:

said operation state detecting means includes warming up state detecting means for detecting a warming up state of said internal combustion engine and operation state change detecting means for detecting a change of said operation state of said internal combustion engine; and said timing varying means includes means for varying said timing for changing over said negative voltage in response to said engine warming up state detected by said warming up state detecting means and means for varying said timing for changing over to said negative voltage in response to said change of said operation state detected by said operation state change detecting means.

6. An apparatus according to claim 5, wherein:

said timing varying means includes means which determines said timing for changing over said negative voltage in response to said engine warming up state for a second set period of time after said internal combustion engine is started and determines said timing for changing over said negative voltage in response to said change of said operation state detected by said operation state change detecting means after said second set period of time.

7. An apparatus according to claim 5, wherein:

said timing varying means includes means for deciding said timing for changing over to said negative voltage by averaging a period determined in response to said engine warming up state and a period determined in response to said change of operation state.

8. An apparatus according to claim 5, wherein:

said timing varying means includes means which determines said timing for changing over said negative voltage in response to said engine warming up state if said change of said engine warming up state exceeds a set value and which determines said timing for changing over to said negative voltage in response to said change of operation state if said change of said engine warming up state is below a second value.

9. An apparatus according to claim 5, wherein:

said warming up state detecting means comprises one of sensor temperature detecting means for detecting a temperature of said oxygen sensor and temperature detecting means for detecting a temperature of said internal combustion engine.

10. An apparatus according to claim 5, wherein:

said operation state change detecting means comprises means for detecting changes of one of an intake air amount, a pressure of intake pipe, a number of rotations of said engine, an air-fuel ratio, a fuel injection amount, a throttle opening angle and a speed of a vehicle associated with said oxygen sensor.

11. An apparatus according to claim 1, wherein:

said oxygen sensor is disposed in an exhaust system of an internal combustion engine, and said timing varying means includes negative voltage application inhibiting means for inhibiting application of said negative voltage if an air-fuel ratio of said internal combustion engine changes more that a set amount.

12. An apparatus according to claim 11, wherein:

said negative voltage application inhibiting means includes load fluctuation detecting means for detecting if a fluctuation of load of the internal combustion engine exceeds a second set value, and timer means for inhibiting said application of said negative voltage for a third set period of time from when said fluctuation of said load has been detected to exceed said second set value till said air-fuel ratio of said internal combustion engine becomes stable.

13. An apparatus according to claim 12, wherein:

said timer means includes stabilizing timing estimating means for estimating a timing from when said fluctuation of said load has varied more than said second set value until said oxygen concentration determined by said oxygen concentration detecting means becomes stable, delay timing estimating means for estimating a delay timing from when said air-fuel ratio at a position where said oxygen sensor is disposed actually changes delaying from said fluctuation of said load, and inhibition determining means for inhibiting application of said voltage during a period time from said delay timing to said stabilizing timing.

14. An apparatus according to claim 12, wherein:

said timer means includes stabilizing timing estimating means for estimating a timing from when said fluctuation of said load has varied more than said second set value till when said oxygen concentration determined by said oxygen concentration detecting means becomes stable, change period estimating means for estimating a period during which an output of said oxygen sensor actually changes delaying from said fluctuation of said load, and inhibition determining means for inhibiting application of said negative voltage during said change period from said stabilizing timing to a point of time before said change period.

15. An apparatus according to claim 1, further comprising:

a heater for heating said oxygen sensor; and heating control means for controlling heating of said heater based on said DC impedance detected by said impedance detecting means.

16. An apparatus according to claim 1, further comprising:

applied voltage varying means for varying said voltage applied to said oxygen sensor based on said DC impedance detected by said impedance detecting means.

17. An oxygen concentration detecting apparatus, comprising:

a current limiting oxygen sensor;

activation determining means for determining whether said oxygen sensor is active;

voltage applying means for applying a positive voltage and a negative voltage to said oxygen sensor, said negative voltage being applied for a set period of time by changing over said voltages if it is determined that said oxygen sensor is active;

negative voltage application continuing means for causing said voltage applying means to continue to apply said negative voltage to said oxygen sensor from a start of an engine associated therewith until said oxygen sensor is determined to be active by said activation determining means;

current detecting means for detecting currents flowing through said oxygen sensor during application of said voltages;

sensor temperature detecting means for detecting a sensor temperature of said oxygen sensor based on said current detected during application of said negative voltage to said oxygen sensor for said set period of time;

oxygen concentration detecting means for detecting an oxygen concentration based on said current detected during application of said positive voltage is applied to said oxygen sensor;

a heater for heating said oxygen sensor; and heating control means for controlling heating of said heater based on said sensor temperature detected by said sensor temperature detecting means.

18. An apparatus according to claim 17, wherein:

said activation determining means includes means for detecting if said sensor temperature detected by said sensor temperature detecting means has reached a temperature sufficient for activating said oxygen sensor.

19. An apparatus according to claim 17, wherein:

said oxygen sensor is disposed in an exhaust system of an internal combustion engine, and said activation determining means includes means for detecting whether a time sufficient for activating said oxygen sensor has passed since a start of said internal combustion engine.

20. An apparatus according to claim 17, further comprising:

sensor temperature stability determining means for determining if said sensor temperature of said oxygen sensor is stable; and period setting means for increasing a period during which said negative voltage is applied to said oxygen sensor if said sensor temperature is determined to be stable by said sensor temperature stability determining means.

21. An apparatus according to claim 20, wherein:

said sensor temperature stability determining means includes means for detecting if said sensor temperature detected by said sensor temperature detecting means has reached a temperature sufficient for stabilizing said sensor temperature.

22. An apparatus according to claim 20, wherein:

said sensor temperature stability determining means includes means for detecting if a variation of said sensor temperature detected by said sensor temperature detecting means is less than a value which corresponds to a stabilization of said sensor temperature.

23. An apparatus according to claim 20, wherein:

said oxygen sensor is disposed in an exhaust system of an internal combustion engine, and said sensor temperature stability determining means includes means for detecting if a time sufficient for stabilizing said sensor temperature has passed since a start of said internal combustion engine.

24. An apparatus according to claim 17, further comprising:

applied voltage varying means for varying the voltage applied to said oxygen sensor on the basis of the sensor temperature detected by said sensor temperature detecting means.

25. An apparatus according to claim 17, further comprising:

impedance detecting means for detecting a DC impedance of said oxygen sensor based on said current detected during application of said negative voltage to said oxygen sensor for said set period of time; and limiting current predicting means for predicting a limiting current occurring after a convergence from said detected current following application of said positive voltage to said oxygen sensor.

26. An apparatus according to claim 25, further comprising:

limiting current detecting means for detecting a current detected after said convergence following application of said positive voltage to said oxygen sensor as said limiting current; and after said detected current after convergence is detected by said limiting current detecting means as said limiting current, said oxygen concentration being determined by said oxygen concentration detecting means based on said detected current after convergence, instead of said predicted limiting current.

27. An apparatus according to claim 26, wherein:

said limiting current detecting means includes means for repeatedly detecting said detected current after an elapse of a second set time sufficient for said detected current to converge following application of said positive voltage to said oxygen sensor as said limiting current.

28. An apparatus according to claim 26, wherein:

said limiting current detecting means includes means for detecting said detected current when said detected current is determined to have not changed substantially since said positive voltage has been applied to said oxygen sensor as said limiting current after said convergence.

29. An apparatus according to claim 25, further comprising:

temperature current predicting means for predicting a current flowing through said oxygen sensor after a convergence by said detected current following application of said negative voltage to said oxygen sensor; and said impedance detecting means includes means for detecting said DC impedance based on said current predicted by said temperature current predicting means.

30. An apparatus according to claim 25, further comprising:

a heater for heating said oxygen sensor and heating control means for controlling heating of said heater based on said DC impedance detected by said impedance detecting means.

31. An apparatus according to claim 25, further comprising:

applied voltage varying means for varying said voltages applied to said oxygen sensor based on said DC impedance detected by said impedance detecting means.

32. An apparatus according to claim 17, further comprising:

timing varying means for variably setting, after said oxygen sensor is determined to be in an activated state, a timing for changing over said voltage applying means to apply said negative voltage to said oxygen sensor such that said change over occurs more frequently as said DC impedance increases.

33. An oxygen concentration detecting apparatus comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of each of said voltages;

impedance detecting means for detecting a DC impedance of said oxygen sensor based on said current detected during application of said negative voltage to said oxygen sensor for said set period of time;

oxygen concentration detecting means for detecting an oxygen concentration based on said current detected during application of said positive voltage to said oxygen sensor; and timing varying means for variably setting a timing for changing over said voltage applying means to apply said negative voltage to said oxygen sensor, wherein said timing varying means includes means for changing said timing to change over said voltage applying means to provide said negative voltage in response to said DC impedance detected by said impedance detecting means, said timing varying means controlling timings for changing over to said negative voltage such that said set period of time becomes longer as a variation of said DC impedance decreases.

34. An oxygen concentration detecting apparatus comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of each of said voltages;

impedance detecting means for detecting a DC impedance of said oxygen sensor based on said current detected during application of said negative voltage to said oxygen sensor for said set period of time;

oxygen concentration detecting means for detecting an oxygen concentration based on said current detected during application of said positive voltage to said oxygen sensor; and timing varying means for variably setting a timing for changing over said voltage applying means to apply said negative voltage to said oxygen sensor, wherein said timing varying means includes means for changing said timing to change over said voltage applying means to provide said negative voltage in response to said DC impedance detected by said impedance detecting means, said timing varying means includes means for changing said timing for changing over to said negative voltage in response to said oxygen concentration detected by said oxygen concentration detecting means, wherein said timing varying means changes over to said negative voltage such that said set period of time becomes longer if said oxygen concentration detected by said oxygen concentration detecting means fluctuates.

35. An oxygen concentration detecting apparatus comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of each of said voltages;

impedance detecting means for detecting a DC impedance of said oxygen sensor based on said current detected during application of said negative voltage to said oxygen sensor for said set period of time;

oxygen concentration detecting means for detecting an oxygen concentration based on said current detected during application of said positive voltage to said oxygen sensor; and timing varying means for variably setting a timing for changing over said voltage applying means to apply said negative voltage to said oxygen sensor, wherein said timing varying means includes means for changing said timing to change over said voltage applying means to provide said negative voltage in response to said DC impedance detected by said impedance detecting means wherein said oxygen sensor is disposed in an exhaust system of an internal combustion engine, and said timing varying means includes negative voltage application inhibiting means for inhibiting application of said negative voltage if an air-fuel ratio of said internal combustion engine changes more that a set amount, said negative voltage application inhabiting means includes:

load fluctuation detecting means for detecting if a fluctuation of load of the internal combustion engine exceeds a second set value, and timer means for inhibiting said application of said negative voltage for a third set period of time from when said fluctuation of said load has been detected to exceed said second set value till said air-fuel ratio of said internal combustion engine becomes stable, said load fluctuation detecting means also detects that at least one of a variation of a throttle opening angle, a pressure of an intake pipe and an intake air amount of said internal combustion engine is more than a fourth set value.

36. An oxygen concentration detecting apparatus comprising:

a current limiting oxygen sensor disposed in an exhaust system of an internal combustion engine;

activation determining means for determining whether said oxygen sensor is active, said activation determining means includes means for detecting whether a time sufficient for activating said oxygen sensor has passed since a start of said internal combustion engine;

voltage applying means for applying a positive voltage and a negative voltage to said oxygen sensor, said negative voltage being applied for a set period of time by changing over said voltages if it is determined that said oxygen sensor is active;

negative voltage application continuing means for causing said voltage applying means to continue to apply said negative voltage to said oxygen sensor until said oxygen sensor is determined to be active by said activation determining means, wherein said time sufficient for activating said oxygen sensor is set to increase as said temperature of said internal combustion engine decreases;

current detecting means for detecting currents flowing through said oxygen sensor during application of said voltages;

sensor temperature detecting means for detecting a sensor temperature of said oxygen sensor based on said current detected during application of said negative voltage to said oxygen sensor for said set period of time;

oxygen concentration detecting means for detecting an oxygen concentration based on said current detected during application of said positive voltage to said oxygen sensor;

a heater for heating said oxygen sensor; and heating control means for controlling heating of said heater based on said sensor temperature detected by said sensor temperature detecting means.

37. An oxygen concentration detecting apparatus comprising:

a current limiting oxygen sensor disposed in an exhaust system of an internal combustion engine;

activation determining means for determining whether said oxygen sensor is active;

voltage applying means for applying a positive voltage and a negative voltage to said oxygen sensor, said negative voltage being applied for a set period of time by changing over said voltages if it is determined that said oxygen sensor is active;

negative voltage application continuing means for causing said voltage applying means to continue to apply said negative voltage to said oxygen sensor until said oxygen sensor is determined to be active by said activation determining means:

current detecting means for detecting currents flowing through said oxygen sensor during application of said voltages;

sensor temperature detecting means for detecting a sensor temperature of said oxygen sensor based on said current detected during application of said negative voltage to said oxygen sensor for said set period of time;

oxygen concentration detecting means for detecting an oxygen concentration based on said current detected during application of said positive voltage to said oxygen sensor;

a heater for heating said oxygen sensor;

heating control means for controlling heating of said heater based on said sensor temperature detected by said sensor temperature detecting means;

sensor temperature stability determining means for determining if said sensor temperature of said oxygen sensor is stable, said sensor temperature stability determining means includes means for detecting if a time sufficient for stabilizing said sensor temperature has passed since a start of said internal combustion engine, wherein said time sufficient for stabilizing said sensor temperature is set to increase as said temperature of said internal combustion engine decreases; and period setting means for increasing a period during which said negative voltage is applied to said oxygen sensor if said sensor temperature is determined to be stable by said sensor temperature stability determining means.

38. An oxygen concentration detecting apparatus, comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of said voltages;

sensor temperature detecting means for detecting a temperature of said oxygen sensor based on said current detected during application of said negative voltage to said oxygen sensor for said set period of time;

oxygen concentration detecting means for detecting an oxygen concentration based on said current detected during application of said positive voltage to said oxygen sensor;

timing varying means for variably setting a timing for changing over said voltage applying means to apply said negative voltage to said oxygen sensor, said timing varying means further comprising means for changing said timing to change said voltage applying means to apply said negative voltage in response to said temperature such that said change over occurs more frequently as said temperature increases;

heater means for heating said oxygen sensor; and heater control means for controlling a heating operation of said heater means in response to said detected temperature of said oxygen sensor.

39. An oxygen concentration detecting apparatus, comprising:

a current limiting oxygen sensor;

voltage applying means for applying a positive voltage and a negative voltage to said oxygen sensor, said negative voltage being applied for a set period of time by changing over said voltages;

current detecting means for detecting currents flowing through said oxygen sensor during application of said voltages;

impedance detecting means for detecting a DC impedance of said oxygen sensor based on said current detected during application of said negative voltage to said oxygen sensor for said set period of time;

limiting current predicting means for predicting a limiting current occurring after a convergence from said detected current following application of said positive voltage to said oxygen sensor;

oxygen concentration detecting means for detecting an oxygen concentration based on said predicted current; and timing varying means for variably setting a timing for changing over said voltage applying means to said negative voltage, including means for changing said timing to change over to said negative voltage in response to said DC impedance detected by said impedance detecting means, wherein said change over occurs more frequently as said DC impedance increases.

40. An oxygen concentration detecting apparatus, comprising:

a current limiting oxygen sensor;

an activation monitor that detects whether said oxygen sensor is active;

a voltage source providing a positive voltage and a negative voltage to said oxygen sensor, said negative voltage being applied for a set period of time by changing over said voltages if it is determined that said oxygen sensor is active;

a control unit that causes said negative voltage application to be continuously provided to said oxygen sensor from a start of an engine associated therewith until said oxygen sensor is determined to be active by said activation monitor;

a current detector that detects currents flowing through said oxygen sensor during application of said voltages;

a temperature sensor unit that detects a temperature of said oxygen sensor based on said current detected during application of said negative voltage to said oxygen sensor for said set period of time;

an oxygen concentration detector that detects an oxygen concentration based on said current detected during application of said positive voltage is applied to said oxygen sensor;

a heater for heating said oxygen sensor; and a heating control unit that control said heater based on said sensor temperature detected by said temperature sensor unit.

41. An oxygen concentration detecting apparatus comprising:

a current limiting oxygen sensor;

a voltage source providing a positive voltage and a negative voltage to said oxygen sensor, said negative voltage being applied for a set period of time by changing over said voltages;

a current monitor that detects currents flowing through said oxygen sensor during application of each of said voltages;

an impedance detector that detects a DC impedance of said oxygen sensor based on said current detected during application of said negative voltage to said oxygen sensor for said set period of time;

an oxygen concentration detecting device that detects an oxygen concentration based on said current detected during application of said positive voltage to said oxygen sensor; and a control unit that variably sets a timing for changing over said voltage source to apply said negative voltage to said oxygen sensor, wherein said control unit changes said timing to change over said voltage source to provide said negative voltage in response to said DC impedance detected by said impedance detector, said change over occurring more frequently as said DC impedance increases.

* * * * *